United States Patent [19]
Kohno et al.

[11] Patent Number: 5,902,398
[45] Date of Patent: May 11, 1999

[54] ARTIFICIAL SEED MANUFACTURING APPARATUS

[75] Inventors: Yasushi Kohno; Takeo Hayashi, both of Shizuoka, Japan

[73] Assignee: Yazaki Corporation, Tokyo, Japan

[21] Appl. No.: 08/724,689

[22] Filed: Oct. 1, 1996

[30] Foreign Application Priority Data

Oct. 3, 1995 [JP] Japan ..................................... 7-256281

[51] Int. Cl.⁶ .............................. B05C 1/02; B05C 11/00; C12M 3/00; C12N 11/04
[52] U.S. Cl. ............................ 118/23; 118/696; 118/697; 435/286.4
[58] Field of Search ........................ 264/4.1, 4.3; 118/13, 118/23, 300, 29, 696, 697; 425/5, 146, 147; 435/286.4

[56] References Cited

U.S. PATENT DOCUMENTS

| | | | |
|---|---|---|---|
| 3,825,235 | 7/1974 | Schwertfeger et al. | 425/146 |
| 4,396,564 | 8/1983 | Stüben et al. | 425/147 X |
| 4,755,123 | 7/1988 | Otake | 425/147 X |
| 4,923,706 | 5/1990 | Binley et al. | 425/146 X |
| 5,512,101 | 4/1996 | Kohno | 118/23 X |
| 5,660,630 | 8/1997 | Kohno | 118/23 |

FOREIGN PATENT DOCUMENTS

| | | |
|---|---|---|
| 62-266137 | 11/1987 | Japan . |
| 63-197530 | 8/1988 | Japan . |
| 3-127920 | 5/1991 | Japan . |
| 5-7016 | 2/1993 | Japan . |

*Primary Examiner*—Richard D. Lovering
*Attorney, Agent, or Firm*—Armstrong, Westerman, Hattori, McLeland & Naughton

[57] ABSTRACT

An artificial seed manufacturing apparatus in which enclosures can be inserted into capsules without fail, and the diameter of the capsule can automatically be controlled. This apparatus comprises: an enclosure supply mechanism with a container, a tip, and a driving source; a coating material delivery mechanism with a passage, a pressure plunger, a hollow nozzle plunger, and a stepping motor; and a control unit for controlling the enclosure supply mechanism and the coating material delivery mechanism, comprising: moving distance storing means for erasably storing setting data which are inputted through setting operation to designate moving distance of the pressure plunger; and stepping motor control means for supplying driving pulse, the stepping motor control means allowing the pressure plunger to reciprocate by the moving distance, to the stepping motor based on the data stored in the moving distance storing means.

8 Claims, 33 Drawing Sheets

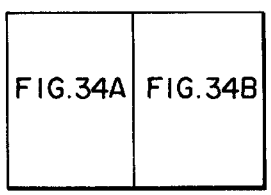

CLEAR NUMBER OF PRODUCT
DEENERGIZE ALL SOLENOIDS OFF
START ROTARY/PRESSURE PLUNGER ORIGIN RESET

| INPUT | STATE | STOP<br>0 | ROTARY/<br>PRESSURE PLUNGER<br>ORIGIN RESET<br>1 | ROTARY ORIGIN<br>RESET<br>2 |
|---|---|---|---|---|
| E1 | START<br>PERSONAL COMPUTER | | 1 | |
| E2 | SUSPENSION | | 16 | 17 |
| E3 | RESTART | | | |
| E4 | END | | ROTARY/<br>PRESSURE<br>PLUNGER<br>FORCED<br>STOPPAGE 0 | ⇐ 0 |
| E5 | SUCTION END<br>SUCTION PROCESS | | | |
| E6 | SUPPLY END<br>SUPPLY PROCESS | | | |
| E7 | ROTATION END<br>ROTATION PROCESS | | 3 | ROTARY<br>DESTINATION = 0<br>TIP = No.1<br>SUCTION START 4 |
| E8 | PRESSURE PLUNGER<br>STOP<br>PRESSURE PLUNGER PROCESS | | 2 | |
| E9 | TIMER STOP<br>TIMER INTERRUPTION | | | |
| E10 | ABNORMALITY<br>DETECTION<br>E5~E8 | ALL<br>OUTPUTS<br>OFF 23 | ⇐ 23 | ⇐ |

FIG.34B

| PRESSURE PLUNGER ORIGIN RESET | | SUCTION | | ROTATION | | INITIAL POSITION | | |
|---|---|---|---|---|---|---|---|---|
| 3 | | 4 | | 5 | | 6 | | 7 |
|  |  |  |  |  |  |  |  |  |
|  | 18 | RETURN EVENT | 4 |  | 17 |  | 17 |  |
|  |  |  |  |  |  |  |  |  |
| ⇐ | 0 | RETURN EVENT | 4 | CHANGE NUMBER OF TARGET | 5 | ⇐ | 6 |  |
|  |  | START ROTATION TIP AT SUCTION END = No.3 → STATE = 6 | 5 |  |  |  |  |  |
|  |  |  |  |  |  |  |  |  |
|  |  |  |  | SUCTION START | 4 | SUCTION START TIP = No.3 SUPPLY START | 8 |  |
| ROTARY DESTINATION = 0 TIP = No.1 SUCTION START | 4 |  |  |  |  |  |  |  |
|  |  |  |  |  |  |  |  |  |
| ⇐ | 23 | ⇐ | 23 | ⇐ | 23 | ⇐ | 23 |  |

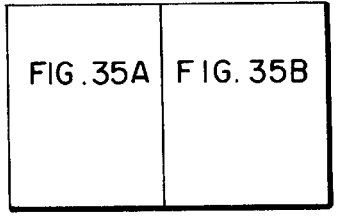

| INPUT \ STATE | | SUCTION/SUPPLY 8 | SUCTION 9 | SUPPLY 10 |
|---|---|---|---|---|
| E1 | START PERSONAL COMPUTER | | | |
| E2 | SUSPENSION | 19 | 20 | 21 |
| E3 | RESTART | | | |
| E4 | END | RETURN EVENT 8 | ⇐ 9 | ⇐ 10 |
| E5 | SUCTION END SUCTION PROCESS | | NUMBER OF PRODUCTS 0→ STATE = 13 START ROTATION 10 | 11 |
| E6 | SUPPLY END SUPPLY PROCESS | | 9 | NUMBER OF PRODUCTS 0→ STATE = 13 START ROTATION 11 |
| E7 | ROTATION END ROTATION PROCESS | | | |
| E8 | PRESSURE PLUNGER STOP PRESSURE PLUNGER PROCESS | | | |
| E9 | TIMER STOP TIMER INTERRUPTION | | | |
| E10 | ABNORMALITY DETECTION E5~E8 | ALL OUTPUTS OFF 23 | ⇐ 23 | ⇐ 23 |

FIG.35B

| ROTATION | TACT WAITING | COMPLETION WAITING | | |
|---|---|---|---|---|
| 11 | 12 | 13 | 14 | 15 |
| | | | | |
| PRESSURE PLUNGER ON → STATE = 16 | 17 PRESSURE PLUNGER ON → STATE = 18 | 0 | 18 | |
| | | | | |
| CHANGE NUMBER OF TARGET | 11 ⇐ | 12 | | |
| | | | | |
| | | | | |
| | 12 | | | |
| | | | 0 | |
| | START SUCTION START SUPPLY | 8 | | |
| ⇐ | 23 ⇐ | 23 ⇐ | 23 | |

FIG. 36

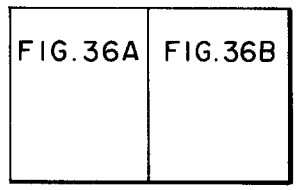

| INPUT | STATE | STOP WAITING ROTARY/PRESSURE PLUNGER ON 16 | STOP WAITING ROTARY ON 17 | STOP WAITING PRESSURE PLUNGER ON 18 | STOP WAITING SUCTION/SUPPLY ON 19 |
|---|---|---|---|---|---|
| E1 | START PERSONAL COMPUTER | | | | |
| E2 | SUSPENSION | | | | |
| E3 | RESTART | | | | |
| E4 | END | | | | |
| E5 | SUCTION END SUCTION PROCESS | | | | 21 |
| E6 | SUPPLY END SUPPLY PROCESS | | | | 20 |
| E7 | ROTATION END ROTATION PROCESS | 18 | 22 | | |
| E8 | PRESSURE PLUNGER STOP PRESSURE PLUNGER PROCESS | 17 | | 22 | |
| E9 | TIMER STOP TIMER INTERRUPTION | | | | |
| E10 | ABNORMALITY DETECTION E5~E8 | ALL OUTPUTS OFF | 23 ⇐ 23 | ⇐ 23 | ⇐ 23 |

TARGET RECALCULATION
ALL CYLINDERS OFF
START ROTARY/PRESSURE
PLUNGER ORIGIN RESET

CLEAR NUMBER OF PRODUCTS
DEENERGIZE ALL SOLENOIDS OFF
START ROTARY/PRESSURE
PLUNGER ORIGIN RESET

| STOP WAITING SUCTION ON | | STOP WAITING SUPPLY ON | | SUSPENSION | | ABNORMALITY | |
|---|---|---|---|---|---|---|---|
| 20 | | 21 | | 22 | | 23 | |
| | | | | | 1 | ← | 1 |
| | | | | | | | |
| | | | | | 1 | ← | 1 |
| | | | | | | | |
| | 22 | | | | | | |
| | | PRESSURE PLUNGER ON → STATE = 18 | 22 | | | | |
| | | | | | | | |
| | | | | | | | |
| | | | | | | | |
| ← | 23 | ← | 23 | ← | 23 | | |

ARTIFICIAL SEED MANUFACTURING APPARATUS

BACKGROUND OF THE INVENTION

1. Field of the Invention

The present invention relates to an artificial seed manufacturing apparatus, and more particularly to an artificial seed manufacturing apparatus which encloses cultured tissues such as adventive embryos into capsules.

2. Description of the Related Art

A conventional artificial seed manufacturing apparatus of this kind is disclosed in Japanese Patent Publication Laid-Open No. Heisei 3-127920, in which cultured tissues such as adventive embryos disperses is enclosed into a gelling agent with a material capable of gelling according to chemical reactions, and liquid droplets of the cultured tissues are supplied through a small hole into hardener, and the liquid droplets during the process of falling are sphericalized by surface tension. In the same Patent Publication, another conventional means continuously protrudes the cultured tissues from a nozzle into hardener to form them in a long string-like shape and cuts them in appropriate lengths.

A technique of Japanese Patent Publication Laid-Open No. Showa 63-197530 moves an end of a hose connected to a sol supply tank in a planetary motion by using a planetary gear to drop sol, which has enclosures dispersed in a coating agent, from the end of the hose into a hardener tank below. A technique of Japanese Patent Publication Laid-Open No. Showa 62-266137 uses centrifugal force to make the liquid droplets.

Of the means disclosed in the Japanese Patent Application Laid-Open No. Heisei 3-127920, the former has a disadvantage that it is difficult to uniformly disperse a number of enclosures in a coating agent, so that the coating materials supplied into the hardener include those that contain the enclosures and those that do not, and these coating materials are mixed, making it necessary to provide a processing for sorting out those coating materials containing the enclosures.

The latter means has a disadvantage that it is extremely difficult to determine the position where the string-like coating materials into blocks are cut and that the number of cultured tissues enclosed in the cut coating blocks becomes unstable.

With the techniques of Japanese Patent Publication Laid-Open Nos. Showa 63-197530 and Showa 62-266137 also, it is difficult to uniformly disperse a number of enclosures.

The cultured tissues as the enclosures, are valuable, so that when the number of enclosures is one, there is no waste but when it is more than one, they may be wasted. The coating blocks without enclosure must be removed by a troublesome selection process. With the above-mentioned methods, it is impossible to make arbitrary changes to the size of the coating materials and the number of enclosures.

With a seed coating apparatus (Japanese Utility Model Publication Laid-Open No. Heisei 5-7016) which coats an enclosure with a film of the coating material, it is possible to change the size of the coat diameter and the number of enclosures arbitrarily. In order to change the size of the coat diameter, however, it is necessary to adjust by manual the amount of coating material to be delivered. This apparatus, therefore, cannot be applied to an artificial seed manufacturing apparatus in which cultured tissues such as adventive embryos generally installed in an aseptic room are enclosed into capsules.

SUMMARY OF THE INVENTION

It is therefore an object of the present invention is to solve the above-mentioned problems and to provide an artificial seed manufacturing apparatus in which enclosures can be inserted into capsules without fail, and the diameter of the capsule can automatically be controlled so as to be suitable for the enclosed cultured tissues, so that the valuable cultured tissues are used without loss, and uniform artificial seeds are contained as well.

Further, in consideration of the above-mentioned problems, another object of the present invention is to provide an artificial seed manufacturing apparatus in which an arbitrary number of enclosures are enclosed into capsule, so that the valuable cultured tissues are used without loss, and uniform artificial seeds are obtained as well.

Still further, in consideration of the above-mentioned problems, another object of the preset invention is to provide an artificial seed manufacturing apparatus in which a capsule without enclosures is not manufactured, so that it is unnecessary to provide a processing for sorting out capsules without enclosures.

To achieve the above-mentioned objects, an artificial seed manufacturing apparatus according to the present invention comprises: an enclosure supply mechanism comprising: a container for accommodating enclosures; a tip for holding one of the enclosures in the container at a holding position and for supplying the enclosure at a supplying position; and a driving source for driving the tip between the holding position and the supplying position; a coating material delivery mechanism comprising: a passage for accommodating a coating material; a pressure plunger slidably inserted into an insertion hole communicating with the passage, the pressure plunger being adapted to pressurize the coating material when moving forward and flowing the coating material into the passage when moving backward; a hollow nozzle plunger for opening a valve by the pressurized coating material to flow the coating material out of the valve, a part of the coating material flown out of the valve drops due to gravity and remainder of the coating material forming film at a lower end portion of the hollow nozzle plunger; and a stepping motor for allowing the pressure plunger to reciprocate through its rotation in both directions; and a control unit for controlling the enclosure supply mechanism and the coating material delivery mechanism, comprising: moving distance storing means for erasably storing setting data which are inputted through setting operation to designate moving distance of the pressure plunger; and stepping motor control means for supplying driving pulse, the stepping motor control means allowing the pressure plunger to reciprocate by the moving distance, to the stepping motor based on the data stored in the moving distance storing means.

It is preferable that the control unit describe above further comprising: rotation control means for causing the tip to move to and stop at the holding position and the supplying position through the driving source; suction control means for allowing the, tip to hold the enclosure in the container at the holding position; and supply control means for supplying the enclosure held by the tip on the film of the coating material through a hollow portion of the hollow nozzle plunger.

In the aforementioned artificial seed manufacturing apparatus, the control unit preferably further comprising number of enclosures storing means for erasably storing setting data which are inputted through setting operation to designate number of enclosures which should be supplied on the film of the coating material, wherein the supply control means supplies the enclosure on the film of the coating material through the hollow portion of the hollow nozzle plunger by the number of enclosures based on the data stored in the number of enclosures storing means; the stepping motor control means supplies the driving pulse, which allows the pressure plunger to reciprocate, to the stepping motor after the supply control means supplies the enclosure on the film of the coating material through the hollow portion of the hollow nozzle plunger by the number of enclosures.

Further, in the artificial seed manufacturing apparatus described above, it is preferable that the supply control means confirms whether or not the tip holds the enclosure prior to supplying motion of the tip at the supplying position; and if the tip does not hold the enclosure, the supply control means cause the tip not to perform the supplying motion at the supplying position but allows following tip to conduct the supplying motion at the supplying position.

In the artificial seed manufacturing apparatus described above, the enclosure may be held by the tip through suction.

In the above-mentioned artificial seed manufacturing apparatus, the enclosures together with culture liquid may be accommodated in the container, and the enclosure may be adventive embryos.

BRIEF DESCRIPTION OF THE DRAWINGS

The present invention will be more apparent from the ensuring description with reference to the accompanying drawings wherein:

FIG. 34 is a view showing a part of state transition which is referred by the CPU in FIG. 14;

FIG. 35 is a view showing another part of state transition which is referred by the CPU in FIG. 14; and FIG. 36 is a view showing a further part of state transition which is referred by the CPU in FIG. 14.

DESCRIPTION OF THE PREFERRED EMBODIMENT

Now, an artificial seed manufacturing apparatus according to an embodiment of the present invention will be explained with reference to drawings.

Figure 1:
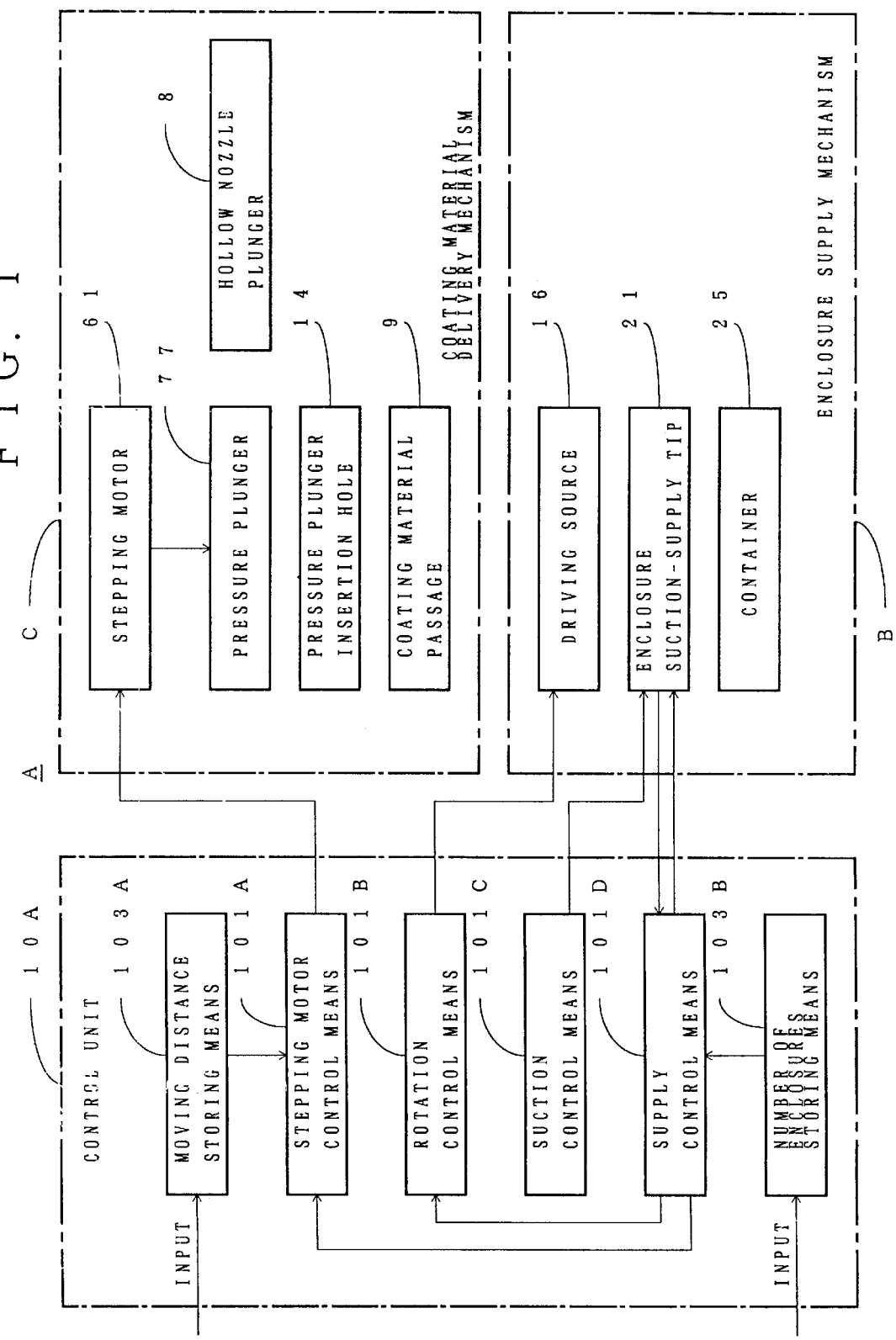
FIG. 1 shows basic configuration of an artificial seed manufacturing apparatus according to the present invention.

FIG. 1 shows basic configuration of an artificial seed manufacturing apparatus according to the present invention.

The artificial seed manufacturing apparatus A comprises: enclosure supply mechanism B, coating material delivery mechanism C, and control unit 10A.

In the enclosure supply mechanism B, a container 25 for accommodating enclosures is provided. An enclosure suction-supply tip 21 sucks one of the enclosure in the container 25 at a sucking position and supplies the enclosure at a supplying position. A driving source 16 drives the tip 21 between the sucking position and the supplying position.

In the coating material delivery mechanism C, a coating material passage 9 is formed, and a pressure plunger 77 is slidably inserted into an insertion hole 14 communicating with the passage 9. The pressure plunger 77 pressurizes the coating material when moving forward and flows the coating material into the passage 9 when moving backward. A hollow nozzle plunger 8 opens a valve by the pressurized coating material to flow the coating material out of the valve and a part of the coating material which is flown out of the valve drops due to gravity. Remainder of the coating material forms film at a lower end portion of the hollow nozzle plunger 8; a stepping motor 61 allows the pressure plunger 77 to reciprocate through its rotation in both directions.

In the control unit 10A for controlling the enclosure supply mechanism B and the coating material delivery mechanism C, moving distance storing means 103A erasably stores setting data which are inputted through setting operation to designate moving distance of the pressure plunger 77. Stepping motor control means 101A for supplies driving pulse, which allows the pressure plunger 77 to reciprocate by the moving distance, to the stepping motor 61 based on the data stored in the moving distance storing means 103A.

Further, in the control unit 10A, rotation control means 101B causes the tip 21 to move to and stop at the sucking position and the supplying position through the driving source 16. Suction control means 101C allows the tip 21 to suck the enclosure in the container 25 at the sucking position. Supply control means 101D supplies the enclosure sucked by the tip 21 on the film of the coating material through a hollow portion of the hollow nozzle plunger 8. A number of enclosure storing means 103B erasably stores setting data, which are inputted through setting operation to designate the number of enclosures that should be supplied on the film of the coating material, so that the supply control means 101D supplies the enclosure on the film of the coating material through the hollow portion of the hollow nozzle plunger 8 by the number of enclosures based on the data stored in the number of enclosures storing means 103B, and the stepping motor control means 101A supplies the driving pulse, which allows the pressure plunger 77 to reciprocate, to the stepping motor 61.

The supply control means 101D described above confirms whether or not the tip 21 sucks the enclosure prior to the supplying motion of the tip 21 at the supplying position. If the tip 21 does not suck the enclosure, the supply control means 101D causes the tip 21 not to perform the supplying motion at the supplying position but allows following tip to conduct the supplying motion at the supplying position.

Figure 2:
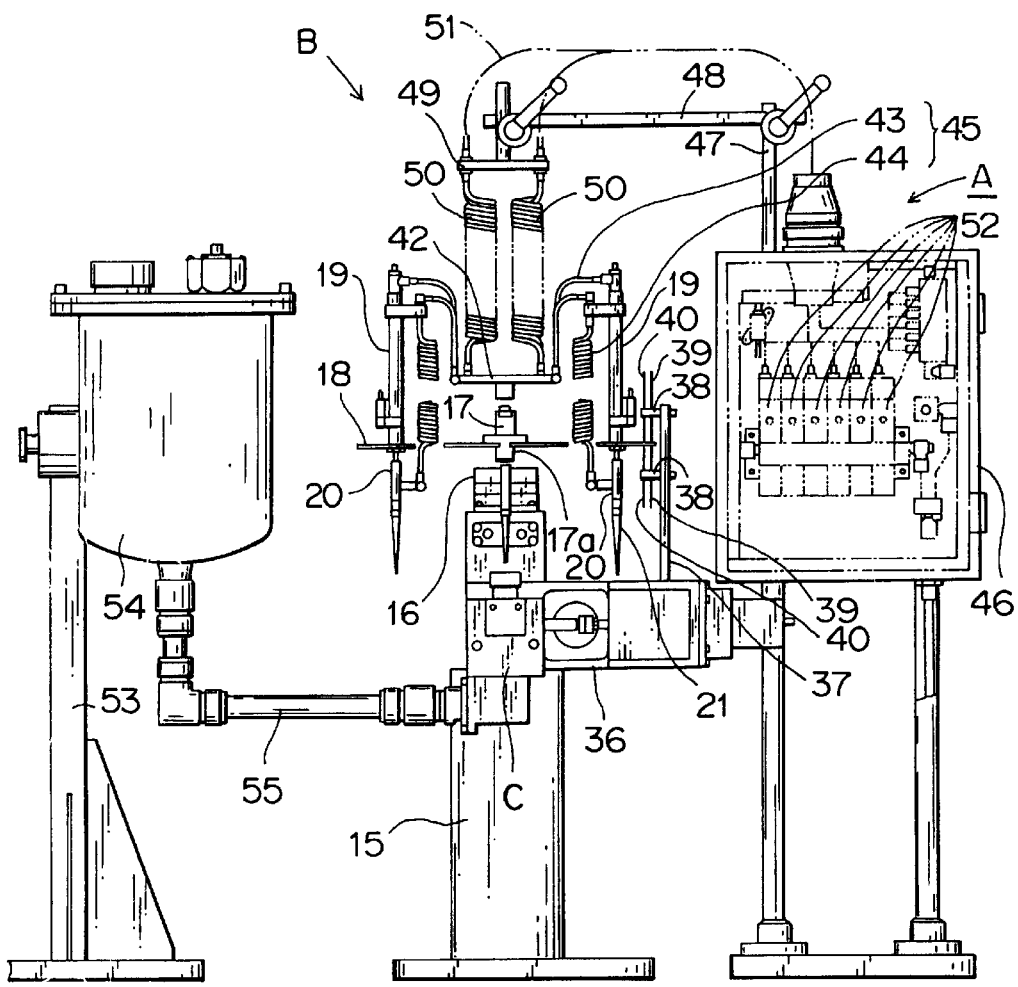
FIG. 2 is a front view of an artificial seed manufacturing apparatus according to an embodiment of the present invention.
Figure 3:
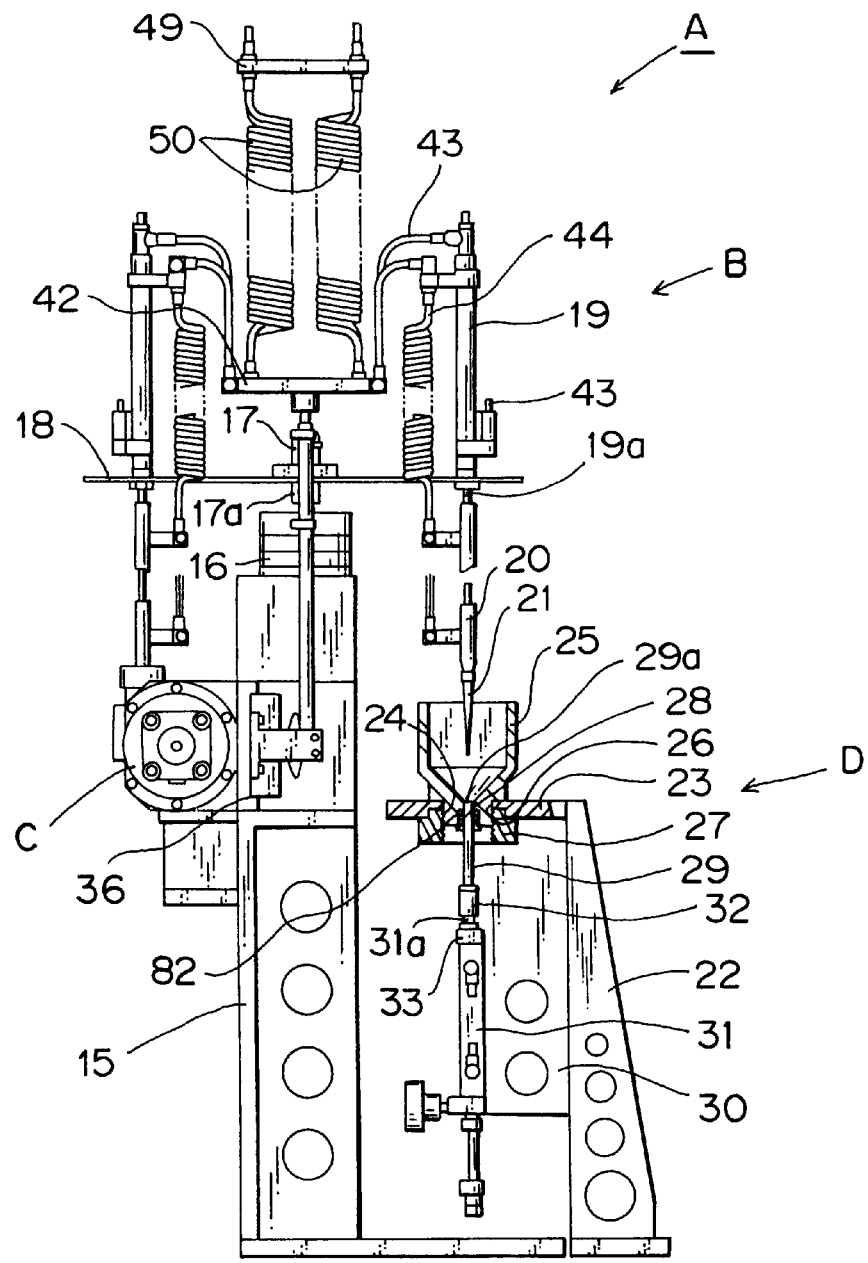
FIG. 3 is a side view of the artificial seed manufacturing apparatus shown in FIG. 2.

As shown in FIGS. 2 and 3, the artificial seed manufacturing apparatus A according to the present invention may be divided into the enclosure supply mechanism B which sucks enclosures such as cultured tissues at suction position and moves the sucked enclosures to supply position for supplying operation, and the coating material delivery mechanism C situated in relation to the supply position. Mounted on the wall surface of a stand 15 located at substantial center of the artificial seed manufacturing apparatus A is a mount 36, to which the coating material delivery mechanism C is fastened by screws. Members composing the enclosure supply mechanism B and the like are installed on the top surface of the stand 15.

Figure 6:
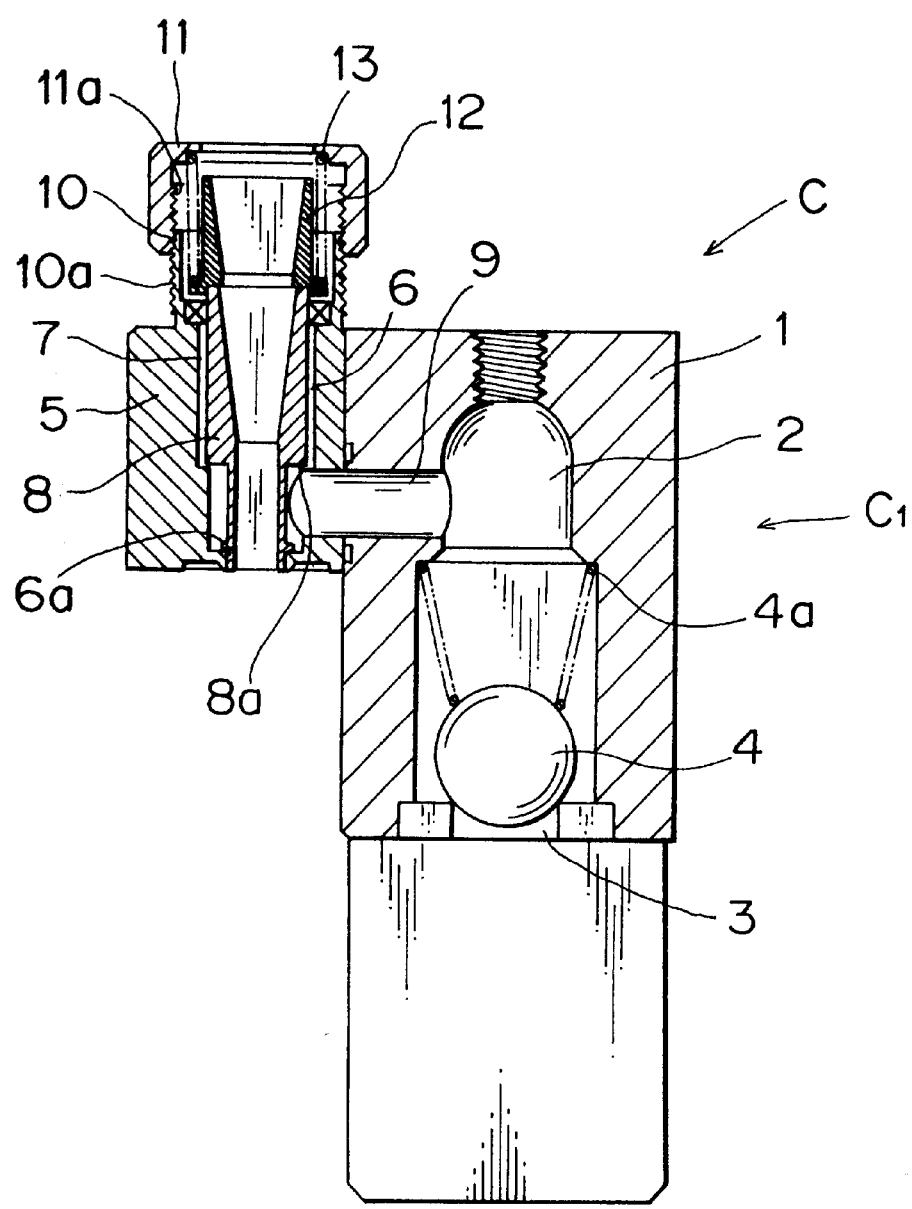
FIG. 6 is a vertical cross-sectional view of a primary portion of a coating material delivery mechanism.
Figure 7:
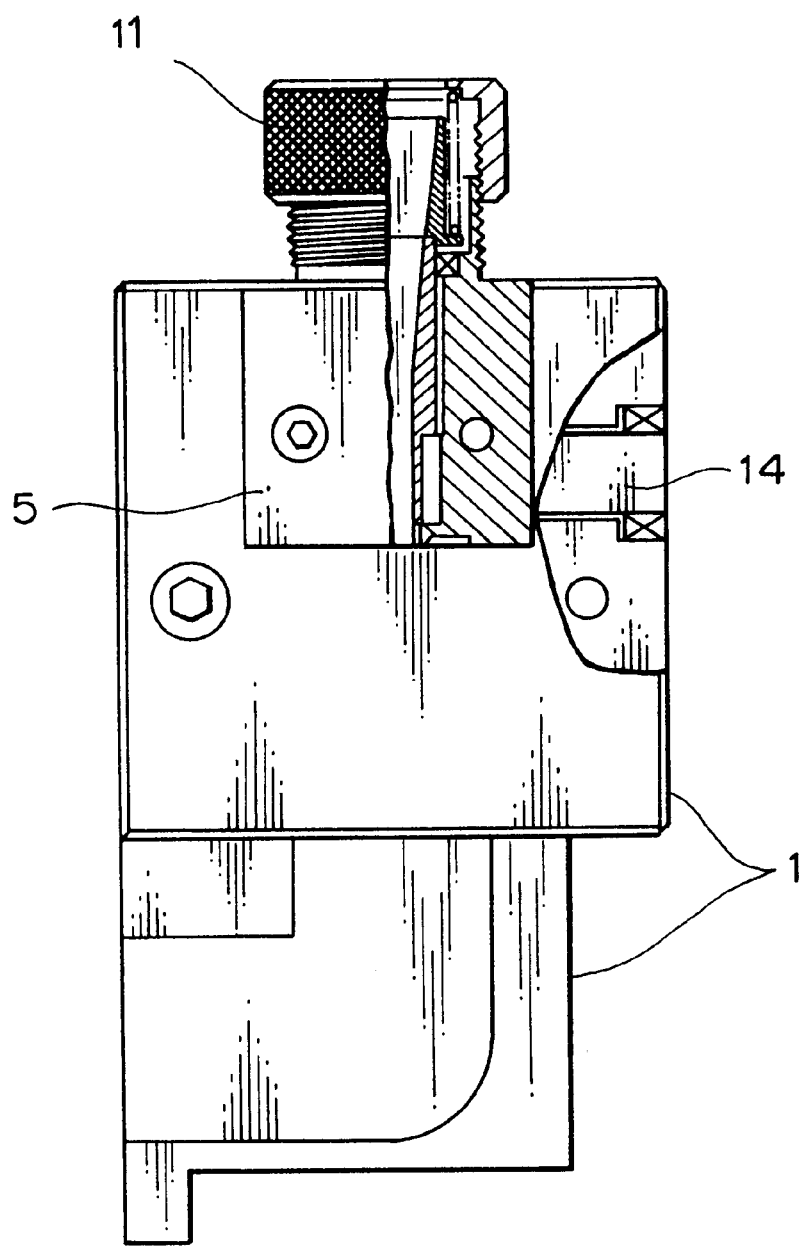
FIG. 7 is a front view of the primary portion of the artificial seed manufacturing apparatus in FIG. 5.
Figure 8:
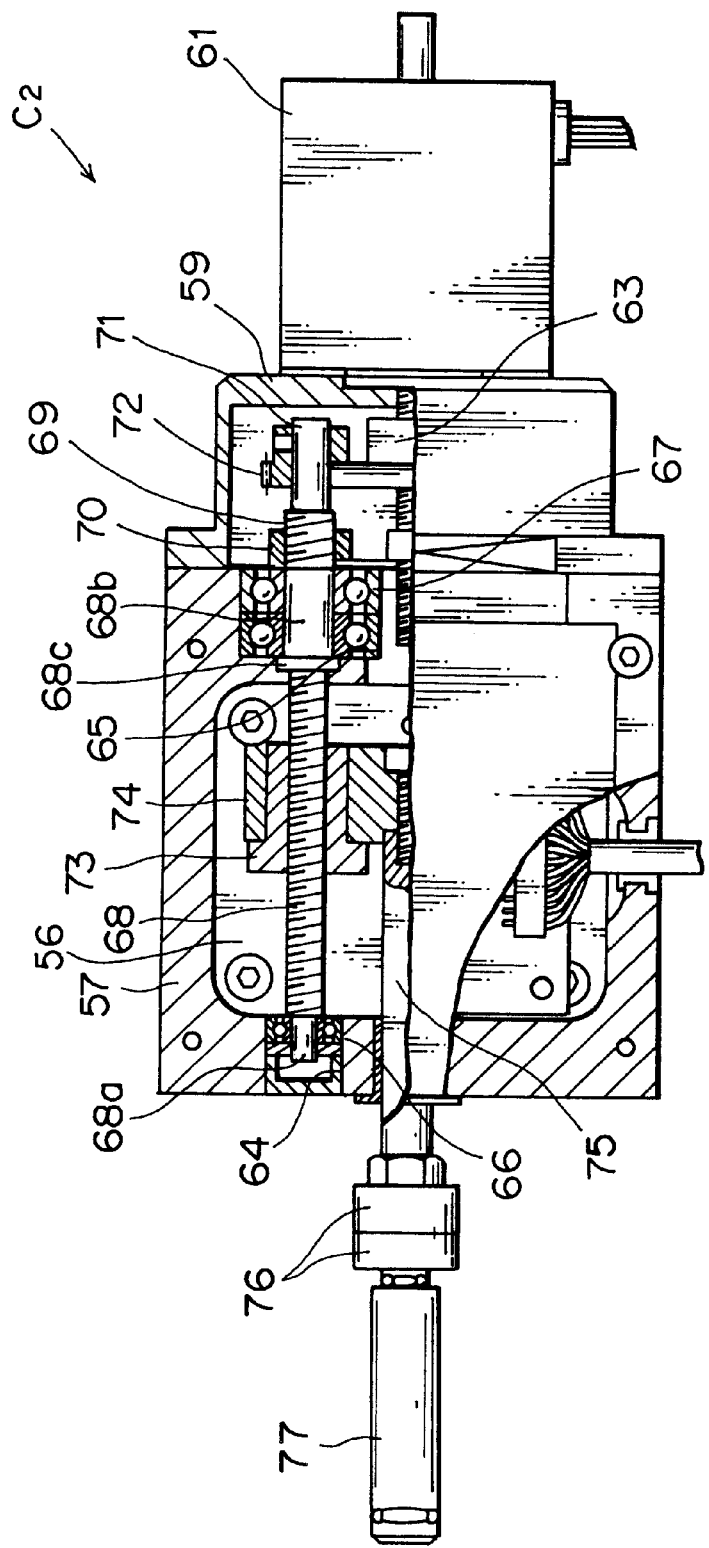
FIG. 8 is a partially cutaway front view of a drive section of the coating material delivery mechanism.
Figure 9:
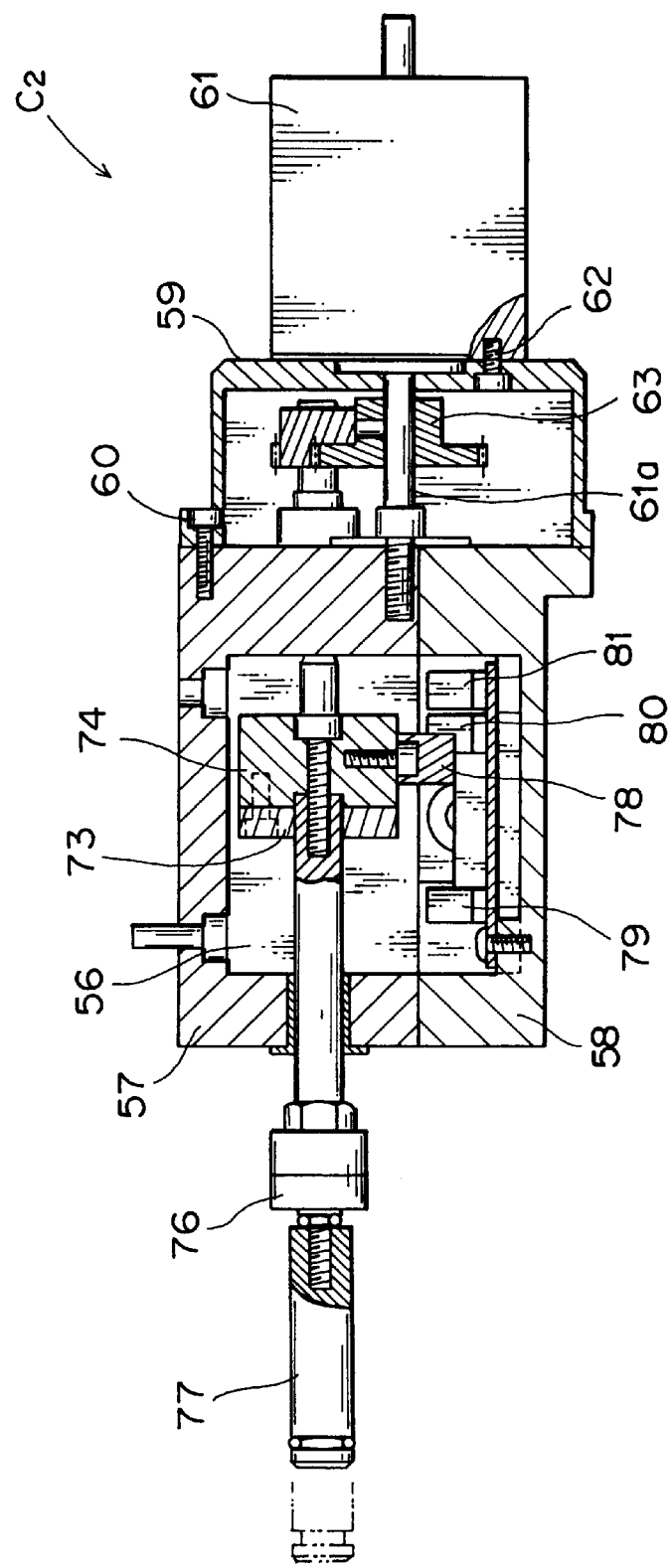
FIG. 9 is a horizontal cross-sectional view of the drive section of the coating material delivery mechanism.
Figure 10:
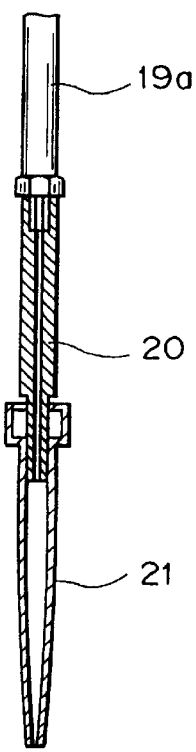
FIG. 10 is a vertical cross-sectional view of an enclosure suction-supply tip.

The coating material delivery mechanism C comprises a valve section C1 shown in FIGS. 6 and 7, a drive section C2 shown in FIGS. 8 and 9, and a coating material tank 54 installed on the left side of FIG. 2. The drive section C2, as shown in FIG. 9, comprises slider cases 57, 58, which are joined together to form a slider accommodating chamber 56 therein, and a gear cover 59 fastened to the right end surface of the slider cases 57, 58 through bolts 60. On the outer surface of the gear cover 59 is secured by bolts 62 a stepping motor 61, whose output shaft 61a has a drive gear 63 rigidly mounted on the outer peripheral surface thereof.

As illustrated in FIG. 8, the slider case 57 is formed with concentric holes 64, 65. The left side hole 64 is fitted with a bearing 66 and the right side hole 65 with a bearing 67. A male screw shaft 68 is rotatably supported by these bearings 66, 67 at a shaft portion 68a formed at its left end and at a shaft portion 68b at its intermediate section. A flange 68C for receiving thrust is provided at the left end of the shaft portion 68b. A nut 70 is screwed over a male screw portion 69 formed on the right-hand side of the shaft portion 68b. The flange 68C and the nut 70 are combined to each other to prevent the male screw shaft 68 from moving in an axial direction thereof.

A shaft portion 71 extending to the right of the male screw portion 69 is fixed with a follower gear 72 in mesh with the drive gear 63. A nut 73 engaged with the male screw shaft 68 is fitted in a hole formed in a slider 74 that is slidable in the slider accommodating chamber 56. The slider 74 is attached with a slide rod 75 that passes through the slider case 57 and an end of the slide rod 75 is fitted with a pressure plunger 77 through a joint 76.

Hence, the rotation of the stepping motor 61 is transmitted through the drive gear 63 and the follower gear 72 to the male screw shaft 68, causing the pressure plunger 77 to move along with the slider 74. As illustrated in FIG. 9, the slider 74 is rigidly fitted with a light shielding plate 78. A stroke end sensor 79, an origin reset position sensor 80 and a stroke end detecting sensor 81 are arranged in a direction that the light shielding plate 78 moves. These sensors 79, 80, 81 are of light emission/reception type. The valve section C1, as shown in FIGS. 6 and 7, has a hollow portion 2 in a substantially rectangular parallele-piped valve body 1. The hollow portion 2 opens to the outside through an insertion hole 14, into which the pressure plunger 77 is slidably inserted. An opening 3 at the lower end surface of the valve body 1 is, as illustrated in FIG. 2, connected with a pipe 55 communicating with the coating material tank 54. As shown in FIG. 6, between the opening 3 and the hollow portion 2 is formed a check valve that consists of a steel ball 4 and a spring 4a for pressing the steel ball 4 toward the opening 3 to open and close the opening 3. A valve case 5 is mounted on the left hand side of the valve body 1.

The valve case 5 has a valve seat 6a formed at the lower end of a plunger insertion hole 6 that vertically passes through the valve case 5. A bushing 7 is fitted to the inner surface of the plunger insertion hole 6, and a hollow nozzle plunger 8 is inserted so at to be vertically movable along the inner surface of the bushing 7. The outer peripheral surface of the nozzle plunger 8 is smaller in diameter at its lower half than the upper half to form a pressure receiving surface 8a. A coating material passage 9 connects the plunger insertion hole 6 and the hollow portion 2 to each other. Coating material is supplied from the coating material tank through the opening 3 and the check valve to the hollow portion 2, and then the coating material is charged into the coating material passage 9 and the plunger insertion hole 6.

Provided on the upper surface of the valve case 5 is a cylindrical portion 10 that surrounds the plunger insertion hole 6. The cylindrical portion 10 has a male screw 10a on its outer peripheral surface, over which is fitted a female screw 11a formed on the inner surface of a spring adjuster 11. On the nozzle plunger 8 is mounted a spring receiver 12, and a spring 13 is mounted between the spring receiver 12 and the spring adjuster 11. As a result, the lower end portion of the nozzle plunger 8 urged downwardly closes the valve seat 6a, however, when the coating material pressure plunger protrudes and raises the pressure of the coating material, the pressure receiving surface 8a of the nozzle plunger 8 is pressed, which in turn causes the nozzle plunger 8 to move upward, opening the valve seat 6a and delivering the coating material.

In FIG. 2, a stay 53 located on the left side is mounted with a coating material tank 54 that accommodates coating material and whose bottom is formed with a hole connected with a coating material transporting pipe 55. An end of the coating material transporting pipe 55 is, as illustrated in FIG. 6, connected to the opening 3 of the coating material delivery mechanism C. When the pressure of the coating material in the coating material passage 9 lowers, the coating material in the tank 54 is supplied into the coating material passage 9.

When the nozzle plunger 8 lowers and closes the valve, the delivery of the coating material stops. But, the coating material adhering to the underside of the valve seat 6a forms into a film covering the lower part of the plunger insertion hole 6 by its surface tension and droops by its own weight. In synchronism with this operation, an enclosure is dropped from the enclosure supply mechanism B described below and is enclosed by the coating material film. When the valve is opened, the enclosure falls down together with the supplied coating material and, during the process of the fall, forms into a sphericalized shape by the surface tension before being supplied to the hardener tank (not shown).

The enclosure supply mechanism B, as shown in FIGS. 2 and 3, is provided with a rotary drive unit 16 including a stepping motor on the upper surface of the stand 15. The rotary drive unit 16 is provided with an output shaft, which is secured to a support member 17. A rotary plate 18 with a hole at the center thereof is sleeved over a small-diameter portion 17a and fastened to the support member 17 by screws. The rotary plate 18 is mounted with air cylinders 19, whose pressure plunger rods 19a are directed downward, at positions that divide the circumference of the rotary plate 18 into six equal parts. An end of each pressure plunger rod 19a is securely connected with a hollow tube 20, whose lower end is attached with an enclosure suction-supply tip 21.

The tip 21 is a cylinder made of a plastic material which is tapered off toward the end. The inner diameter of the end of the suction tip is made in such a manner that a single enclosure is to be drawn. When the kind of enclosure to be processed is changed, the tip 21 is replaced with one having an appropriate diameter in accordance with the dimension of the enclosure. It is convenient since the tip 21 can easily be attached to or detached from the hollow tube 20 due to its elasticity.

The enclosure supply mechanism B is provided with a bracket 23 mounted on the top of a stay 22, which is installed on a side opposite to the coating material delivery mechanism C with respect to the output shaft of the rotary drive unit 16. The bracket 23 has a slot 24 opening to its side, in which a small-diameter portion 26 at the lower part of an enclosure container 25 is movably inserted as illustrated FIG. 3. The small-diameter portion 26 has a male screw, and the enclosure container 25 is fixed to the bracket 23 through a lock handle 27 with a female screw that engages with the male screw.

The enclosure container 25 opens at the top and contains a culture liquid in which a number of enclosures such as adventive embryos are immersed. At the bottom, the enclosure container 25 has a through-hole 28 extending through the small-diameter portion 26. In a groove formed in the inner periphery of the small-diameter portion 26 around the through-hole 28 is fitted a water-tight seal 82 that seals the gap between the small-diameter portion 26 and the supply rod 29, which is vertically movably inserted into the through-hole 28. In this embodiment, an O-ring is used as the water-tight seal 82.

A supply rod actuator 31 is mounted on a cylinder stand 30 which is fixed to the side of the stay 22. As the supply rod actuator 31, an air cylinder is used. The upper end of an upwardly acting piston rod 31a is formed with a male screw, with which engage a threaded hole formed at the lower end surface of a joint 32 and a nut 33 that fixes the joint 32 (see FIGS. 3 and 13).

Figure 11:
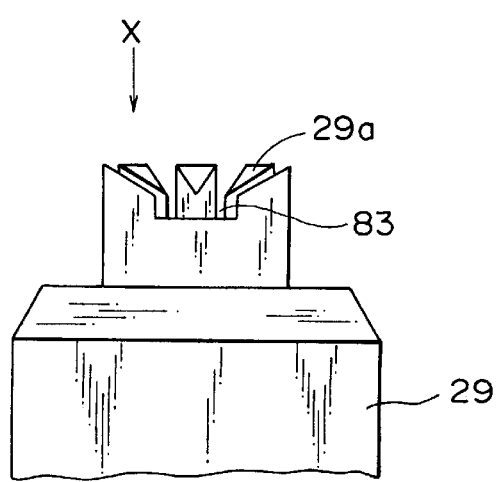
FIG. 11 is a front view of a primary portion of a supply rod.
Figure 12:
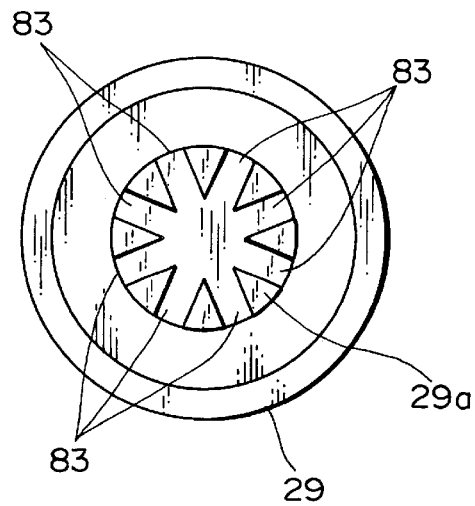
FIG. 12 is a view as seen from an arrow X in FIG. 11.
Figure 13:
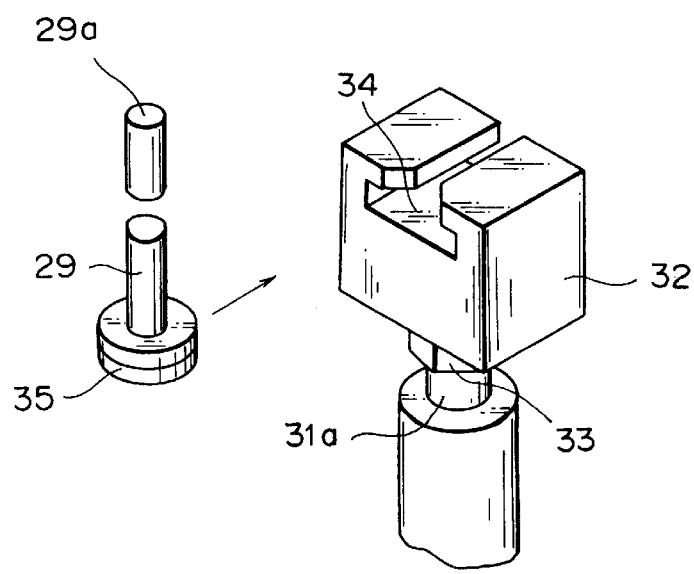
FIG. 13 is a perspective view showing a connection between the supply rod and the enclosure suction-supply rod.

As illustrated in FIGS. 3 and 13, upper surface of the joint 32 is formed with a T-shaped groove 34 extending in parallel to the slot 24. The lower end of the supply rod 29 inserted into the through-hole 28 is formed into a T shape in cross section to provide a T-shaped portion 35 that can be removably inserted into the T-shaped groove 34. As illustrated in FIGS. 11 and 12, the upper surface of the supply rod 29 is formed with a recessed enclosure mounting surface 29a, which in turn is provided with a plurality of radially extending liquid discharge grooves 83.

Figure 5:
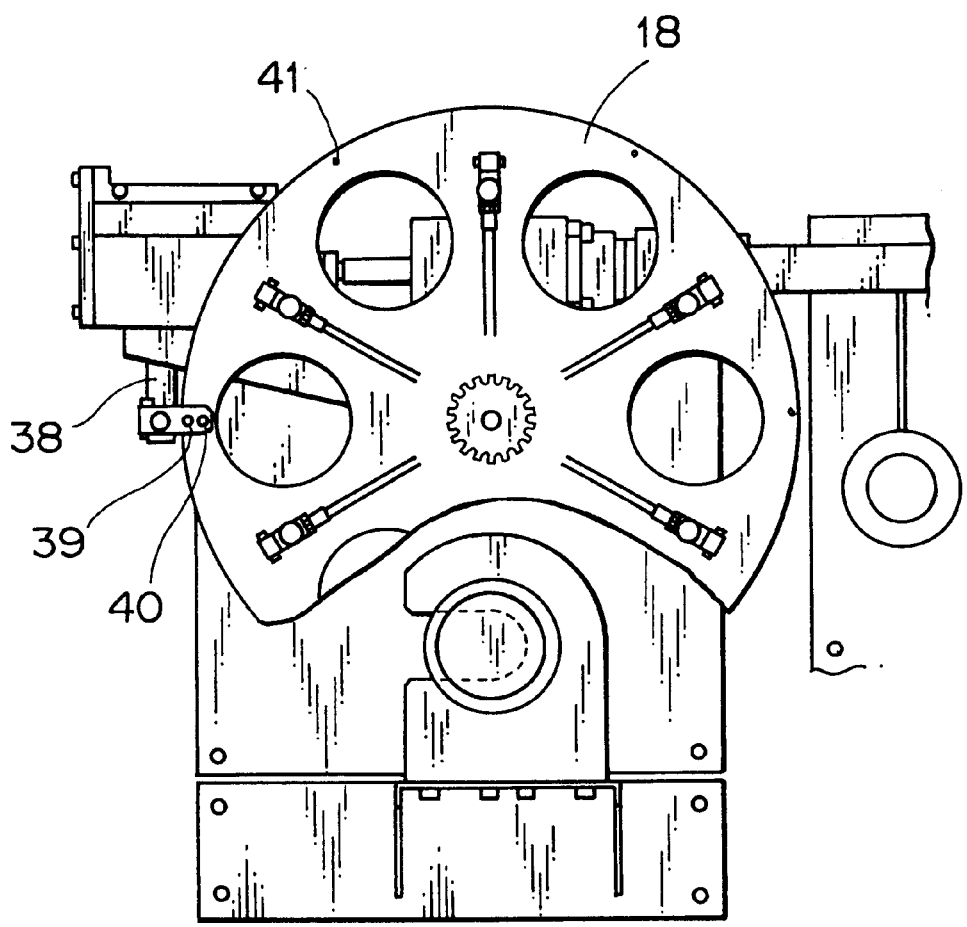
FIG. 5 is a partially cutaway plan view of the artificial seed manufacturing apparatus in FIG. 3.

As shown in FIG. 2, a sensor support pillar 37 erected on the mount 36 is securely attached at two vertically separate locations with arms 38. The arms 38 are each provided with a pair of position sensor 39 and origin reset sensor 40 with light emitting and receiving portions at top and bottom. As illustrated in FIG. 5, the rotary plate 18 is provided at its outer periphery with positioning small holes 41 that divide the circumference of the rotary plate 18 into six equal parts and one reset timing small hole (not shown). When the position sensor 39 detects the positioning small holes 41, a stop signal for the plate 18 is transmitted. When the origin reset sensor 40 detects the reset timing small hole 41, an origin reset signal is transmitted.

As illustrated in FIG. 2, the upper end of the support member 17 is fixedly fitted with a rotary manifold 42, which has an air pressure tube 43 connected to two vertically separate ports of each air cylinder 19 for each tip and a tip side tube 45 formed of a tube 44 that supplies an air pressure or negative pressure to the hollow tube 20. A control panel 46, which is installed on the right-hand side and incorporates a control circuit, has a support rod 47, which is securely fitted with a side rod 48 that has a stationary manifold 49 at an end thereof.

The stationary manifold 49 is located above the rotary manifold 42. The rotary manifold 42 and the stationary manifold 49 are connected to both ends of elastic tubes 50, which are coiled and slightly deformable. A stationary side pipe 51 running from the stationary manifold 49 to the control panel 46 communicates through a selector valve 52 in the control panel 46 with an air pressure source and a negative pressure source (not shown).

Figure 14:
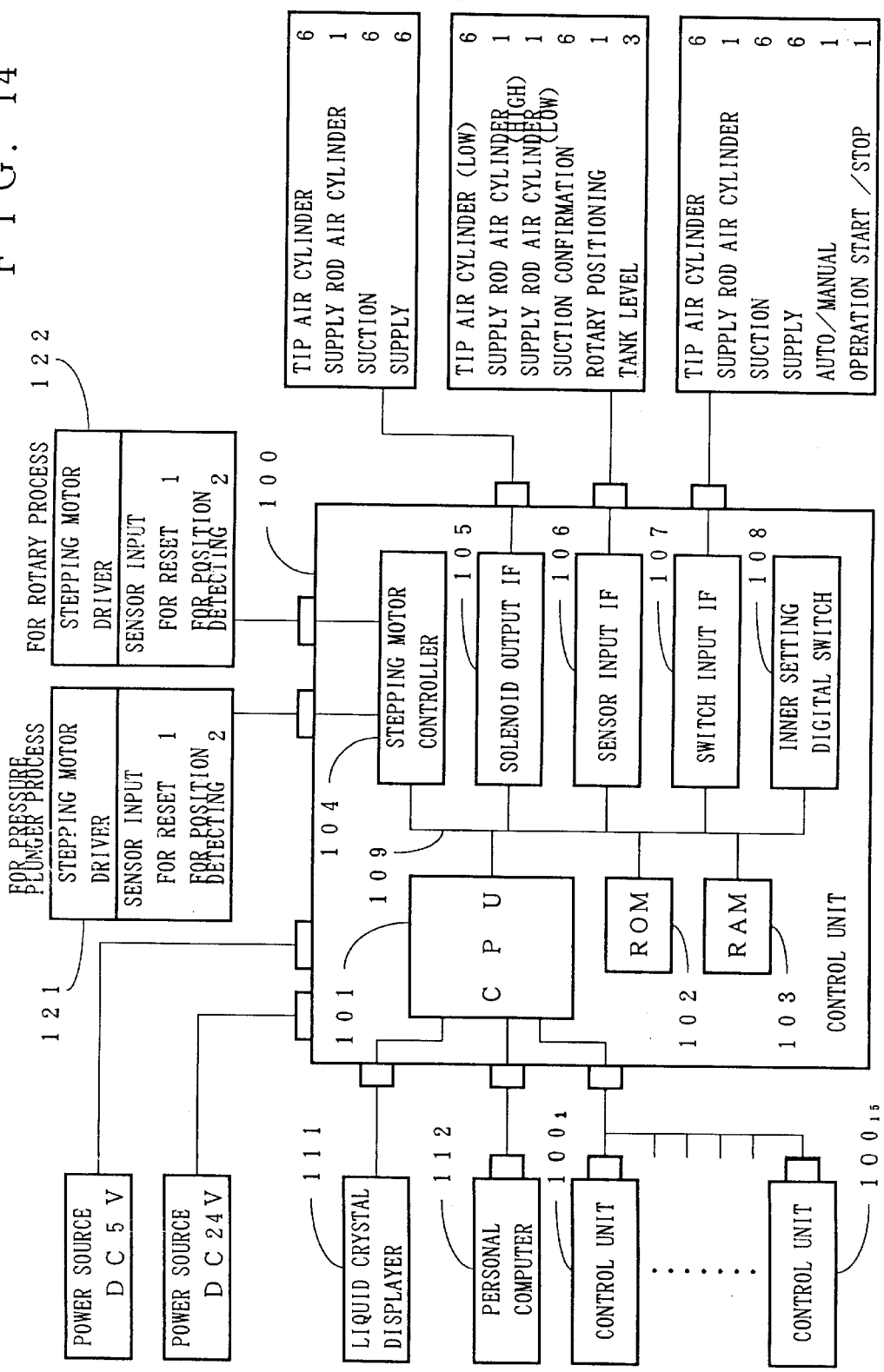
FIG. 14 shows the configuration of a control unit of the artificial seed manufacturing apparatus according to the present invention.

Next, a control unit of the artificial seed manufacturing apparatus with the above-mentioned construction will be explained with reference to FIG. 14 illustrating circuit configuration of the unit. In the figure, numeral 100 is a control unit which comprises a central processing unit (hereinafter referred to as "CPU") 101 operated in accordance with predetermined programs, a read only memory (ROM) 102, a random access memory (RAM) 103, a stepping motor controller 104, a solenoid output interface 105, a sensor input interface 106, a switch input interface 107 and an inner setting digital switch 108. Those devices are connected to each other through a bus 109.

A liquid crystal displayer 111 is connected to the CPU 101 with a connector. The liquid crystal displayer 111 displays state of the motion as well as results and target of the manufacturing. When abnormality is detected, the content of the abnormality is also displayed, and during manual operation, this state is also displayed on the liquid crystal displayer 111. To the CPU 101 may be connected a personal computers 112 with a connecter in conformity to RS232C, and control units, at most 15 units, 1001 to 10015 through connectors in conformity to RS485.

The personal computer 112 is used to set parameters, which are used for the control at the control unit 100, such as the number of products, the number of enclosures to be enclosed, working velocity, time for the supply solenoid ON, timing of the movement of the pressure plunger, distance that the pressure plunger moves, time for movement of the pressure plunger, and the number of retries of suction.

The number of manufacturing target is used for stopping the artificial seed manufacturing apparatus A when the actual number of products reaches this number. The number of enclosures to be enclosed means the number of enclosures which are inserted into the coating agent, and when the number of enclosures reaches this number, the pressure plunger moves, that is, the pressure plunger protrudes coating material. The working velocity is set to determine the number of enclosures to be enclosed per one hour. The time for supply solenoid ON indicates the period of time that the positive air solenoid is energized at supply operation, and rotary/pressure plunger processes are not be operated during this period. The timing of the movement of the pressure plunger indicates the period of time from the completion of the supply operation to the start of the movement of the pressure plunger. The pressure plunger moving distance is defined as the length that the coating material protrudes at the operation of the pressure plunger. The pressure plunger moving time is a period of time required for the movement of one way (protrusion or drawing), which causes the motor to be driven so that the pressure plunger moves by the distance, which is set as "pressure plunger moving distance", for the pressure plunger moving time. The number of suction retries are the number that is repeated at the failure of the suction operation.

The stepping motor controller 104 comprises a stepping motor driver 121 for driving the stepping motor 61 which causes the pressure plunger 77 of the coating material delivery mechanism C to reciprocate; three sensors such as the origin reset position detecting sensor 80 and the stroke end detecting sensor 79 and 81, for detecting positions of the pressure plunger 77 which reciprocates due to the rotation of the stepping motor 61, the three sensors 80, 79, 81 being connected to each other with a single connector; the stepping motor driver 122 for driving the stepping motor 61 which rotates the rotary plate 18 of the enclosure supply mechanism B in both directions; and three sensors, such as the origin reset sensor 40 and two position detection sensors 39, for detecting the rotational position of the rotary plate 18 which is driven by the stepping motor 61, the three sensors 40, 39, 39 being connected to each other with a single connector.

The solenoid output interface 105 comprises: six tip air cylinder solenoids which drive the tip air cylinders 19 at positions that divide the circumference of the rotary plate 18 into six equal parts when the solenoids are energized; a supply rod air cylinder solenoid for raising the supply rod 29 of the enclosure supply mechanism B when the solenoid is energized; six suction solenoids for applying negative pressure to the tip 21, which rises or falls due to the movement of the tip air cylinder 19, so as to suck the enclosures; and six supply solenoids for applying a pressure to the tip 21 so as to supply the enclosures. The above solenoids are connected with each other with a single connector.

The sensor input interface 106 comprises: six lower position detecting sensors and an upper position detecting sensor for detecting the lower position and the upper position of the tip air cylinder 19 attached to the rotary plate 18 respectively; an upper position detecting sensor and a lower position detecting sensor for detecting the upper position and lower position of the supply rod 29 which rises and falls due to the movement of the supply rod air cylinder 31 respectively; six suction confirming sensors for confirming through the transition of the negative pressure that the tip 21, to which applied a negative pressure, sucks the enclosures; a rotational positioning detecting sensor for detecting the positioning of the stepping motor 61 which rotates the rotary plate 18; and three tank level detecting sensors for detecting the level of the coating material in the coating material tank 54 such as high level, middle level and low level. Those sensors are connecter to each other with a single connector.

The switch input interface 107 is connected to several switches which are operated at manual operation. That is, six tip air cylinder switches (not shown) which are operated to drive the tip air cylinder 19 mounted to the rotary plate 18; the supply rod air cylinder switch which is operated to drive the supply rod air cylinder 31 for raising and lowering the supply rod 29 of the enclosure supply mechanism B; suction switches which are operated to cause the tip 21 to suck the enclosures; supply switches which are operated to supply the enclosures sucked by the tip 21; and auto/manual switch which is operated to change the operation between auto and manual; and start/stop switch which is operated to start and stop the operation through manual operation. Those switches are connected to each other with a single connector.

The construction of the artificial seed manufacturing apparatus is described above. Next, the motion of the enclosure supply mechanism B, in which the tip 21 sucks the enclosures at the enclosure suction position on the side of the enclosure container 25 and supplies the sucked enclosures are supplied at the enclosure supply position on the side of the nozzle plunger 8, will be explained below with reference to FIGS. 15 to 22 of state transition diagrams which show the order that the rotary plate 18 of the enclosure supply mechanism B is positioned and FIGS. 23 to 33 of flow charts indicating the process performed by the CPU 101 of the control unit 100.

Figure 15:
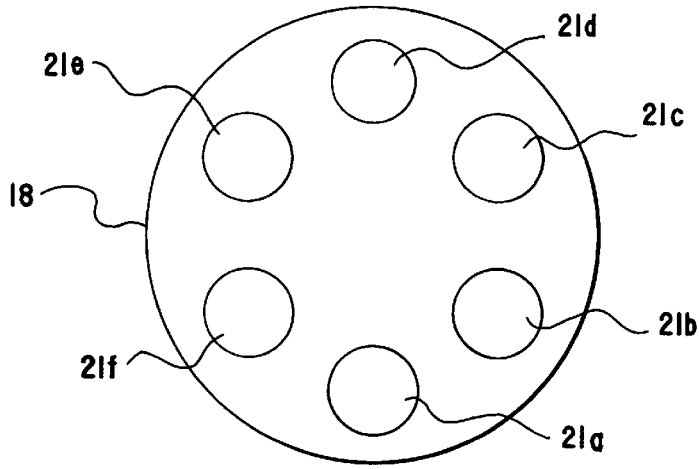
FIG. 15 is view for explaining a state of the enclosure suction-supply tips immediately after initial positioning.
Figure 16:
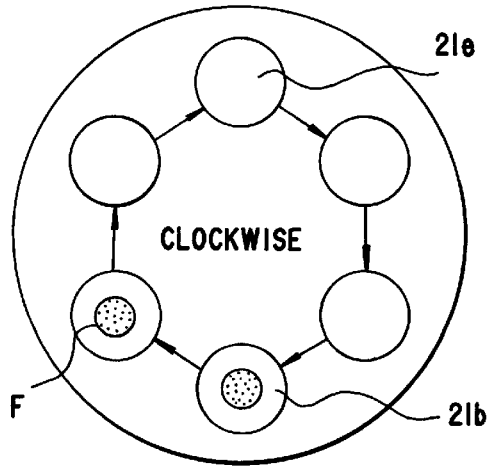
FIG. 16 is a view for explaining a state during an initial suction process.
Figure 17:
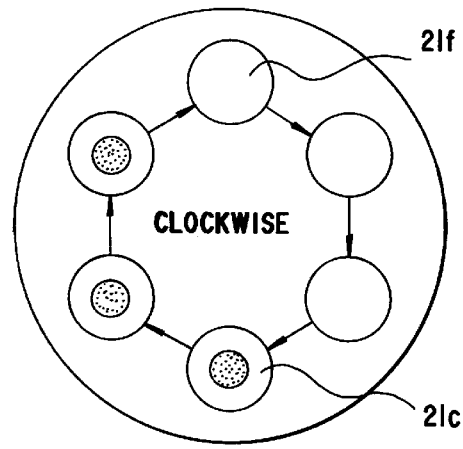
FIG. 17 is a view for explaining a state at the completion of the initial suction process.

At the suction and supply processes of the enclosure supply mechanism B, at first, the CPU 101 of the control unit 100 confirms the initial positions of the piston stepping motor and rotary stepping motor and clogging of the tip 21. FIG. 15 shows a state of the rotary plate 18 when the confirmation procedures of the initial positioning are finished. The suction and supply of enclosures start from the above-mentioned state. FIGS. 15 to 17 illustrate initial suction processes.

In FIG. 15 showing the initial position of the rotary plate 18, the lower side of the rotary plate 18 is defined as an enclosure suction position and the upper side thereof as an enclosure supply position. Six tips mounted to the rotary plate 18 are symbolized as 21a to 21f. When the rotary plate 18 is positioned at the initial position, the tip 21a is located directly above the supply rod 29 of the enclosure container 25 and the tip 21d directly above the nozzle plunger 8 of the enclosure supply mechanism B.

In the initial suction operation, the stepping motor 61 rotates the rotary plate 18 clockwise to protrude the tip air cylinder, and the supply rod air cylinder protrudes to perform suction motion, which causes the tips 21a to 21c to suck the enclosures F as illustrated in FIGS. 15 to 17 (shown as black dots in the figures). In other words, in FIG. 15, when negative pressure is applied to inside of the tip 21a to suck an enclosure, the tip 21a is increased in negative pressure therein. The pressure is detected by a negative pressure sensor (not shown) to confirm the suction of the enclosures. When this suction is not confirmed, the tip air cylinder and the supply rod air cylinder are drawn and the protrusion of the air cylinders are performed again. When a signal from the negative pressure sensor confirms that the suction is successfully completed, the rotary plate 18 rotates clockwise in FIG. 15 together with the stepping motor 61. The rotary plate 18 is rotated after it is confirmed that the air cylinders are drawn.

Then, when the positioning sensor 39 detects the positioning small holes 41 on the rotary plate 18, the stepping motor 61 stops to position the tip 21b directly above the supply rod 29 and the tip 21e directly above the nozzle plunger 8 respectively. At the positions, the enclosure F is sucked by the tip 21b in the same manner as described above. Then, the rotary plate 18 is rotates clockwise by 60 degrees and stops there as illustrated in FIG. 17, and the enclosure F is sucked by the tip 21c directly above the supply rod 29 to complete the suction operation.

Figure 18:
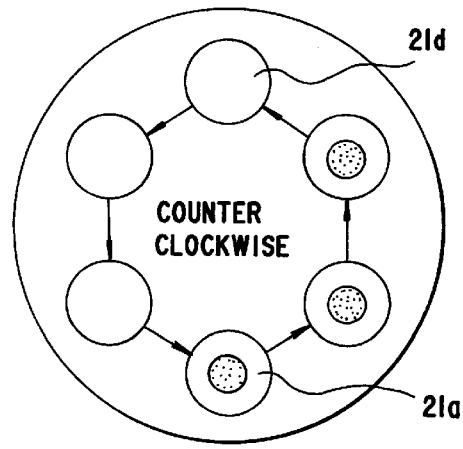
FIG. 18 is a view for explaining a state when the process returns to an initial position.

When the suction process is finished, the initial position reset sensor 40 detects the reset timing small hole (not shown), which causes the stepping motor 61 to rotate the rotary plate 18 counterclockwise and, as illustrated in FIG. 18, to return the rotary plate 18 to the original position corresponding to the state shown in FIG. 15, and the initial suction process is completed. As a result, twist generated at the elastic tubes 50 are released. As described above, after the stepping motor 61 is rotated counterclockwise by 120 degrees to return the rotary plate 18 to the original position, the stepping motor 61 is further rotated counterclockwise by 60 degrees to obtain the state illustrated in FIG. 19.

Figure 19:
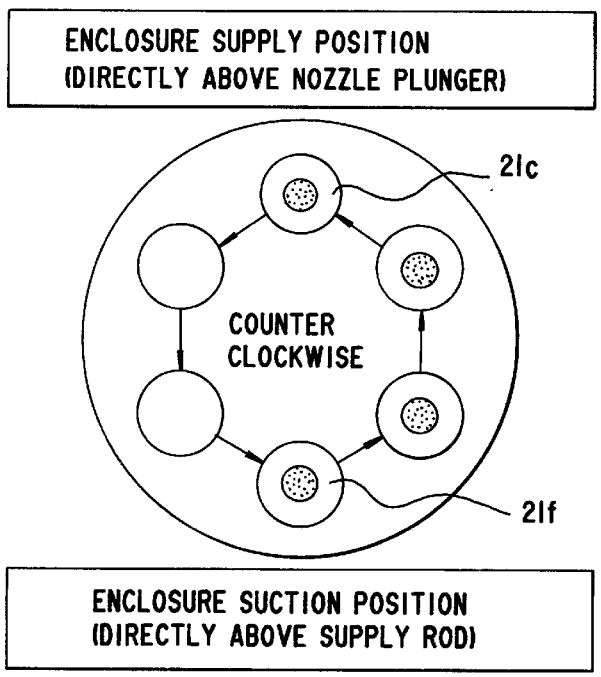
FIG. 19 is a view for explaining a state during operation of the artificial seed manufacturing apparatus.

In the state shown in FIG. 19, following motions are performed on the enclosure supply position side and the enclosure suction position side. At the enclosure supply position directly above the nozzle plunger 8, the suction by the tip 21c is confirmed, and the confirmation is finished, that is, the suction is successfully performed, the tip air cylinder is protruded to pressurize inside of the tip 21c and to blow air into the tip 21c, which allows the enclosure F to be supplied on the film of the coating material on the nozzle plunger 8 and causes the stepping motor 61 to be driven. At the enclosure suction position directly above the supply rod 29, the tip air cylinder and the supply rod air cylinder 31 are protruded and the suction by the tip 21f is applied, and this motion is confirmed. After the completion of the motions on the enclosure supply side and the enclosure suction side, the stepping motor 61 is rotated counterclockwise by 60 degrees to obtain the state shown in FIG. 20.

Figure 20:
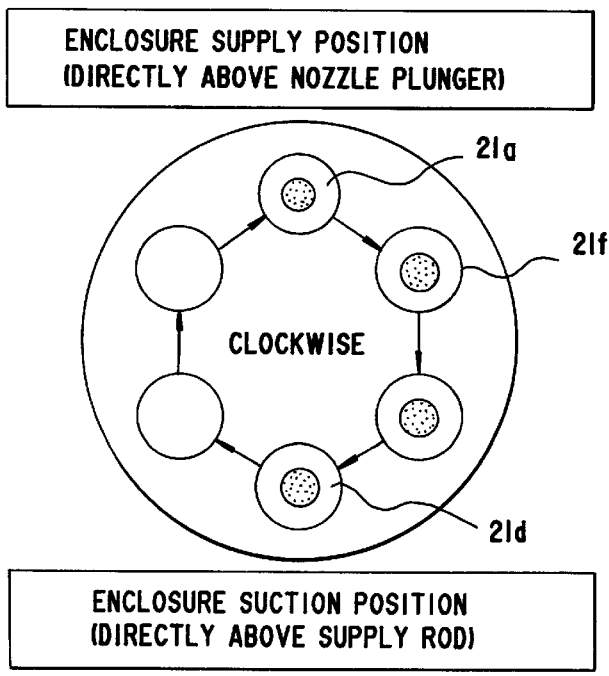
FIG. 20 is a view for explaining a state during a reverse operation of the artificial seed manufacturing apparatus.

In the state shown in FIG. 20, following motions are performed on the enclosure supply side and the enclosure suction side. On the enclosure supply side, the suction of the tip 21a is confirmed. When the confirmation is finished, the tip air cylinder is protruded to pressurize inside of the tip 21a and to blow air into the tip 21a, which allows the enclosure F to be supplied on the film of the coating material on the nozzle plunger 8 and causes the stepping motor 61 to be driven. At the enclosure suction position directly above the supply rod 29, the tip air cylinder is protruded and the suction by the tip 21d is carried out, and this motion is confirmed. After the completion of the motions on the enclosure supply side and the enclosure suction side, the stepping motor 61 is further rotated counterclockwise by 180 degrees to obtain the state shown in FIG. 21.

Figure 21:
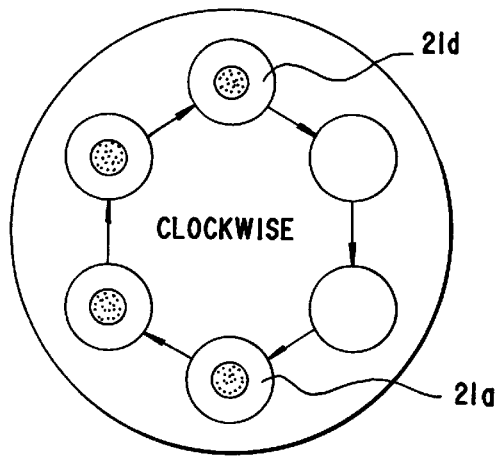
FIG. 21 is a view for explaining a state immediately after the reverse operation in FIG. 20.

In the state shown in FIG. 21, on the enclosure supply side, the suction of the tip 21d is confirmed. When the confirmation is finished, the tip air cylinder is protruded to pressurize inside of the tip 21d and to blow air into the tip 21d, which allows the enclosure F to be supplied on the film of the coating material on the nozzle plunger 8 and causes the stepping motor 61 to be driven. On the enclosure suction side, the tip air cylinder and the supply rod air cylinder 31 are protruded and the suction by the tip 21a is carried out, and this motion is confirmed. After the completion of the motions on the enclosure supply side and the enclosure suction side, the stepping motor 61 is further rotated counterclockwise by 180 degrees to obtain the state shown in FIG. 22.

At that moment, the origin reset sensor 40 detect the reset timing small hole (not shown) on the rotary plate 18 to stop the rotary plate 18, and the twist of the elastic tubes 50 in a direction opposite to the rotation of the rotary plate 18 are released. As described above, the rotation of the rotary plate 18 is not accumulated, so that the twist of the elastic tubes 50 is restricted and the excess force is not applied to the elastic tubes 50 which are wound like a coil and are easily deformed by torsion.

Figure 22:
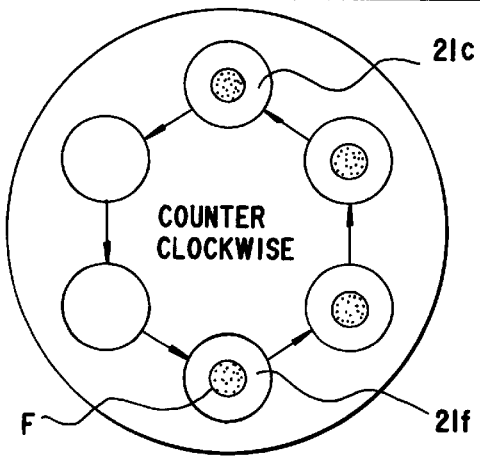
FIG. 22 is-a view for explaining a state immediately after the reverse operation.

In the state illustrated in FIG. 22, on the enclosure supply side, the suction of the tip 21c is confirmed. When the confirmation is finished, the tip air cylinder 19 is protruded to pressurize inside of the tip 21c and to blow air into the tip 21c, which allows the enclosure F to be supplied on the film of the coating material on the nozzle plunger 8 and causes the stepping motor 61 to be driven. On the enclosure suction side, the tip air cylinder 19 and the supply rod air cylinder 31 are protruded and the suction by the tip 21f is carried out, and this motion is confirmed. After the completion of the motions on the enclosure supply side and the enclosure suction side, the stepping motor 61 is further rotated counterclockwise by 60 degrees, and hereinafter the above steps are repeated.

When it is confirmed that the suction of the tip on the enclosure supply side is insufficient, the blow in the tip and the motion of the pressure plunger stepping motor are skipped. In the above-mentioned embodiment, only one enclosure is enclosed, and when the number of enclosures to be enclosed is changed, the artificial seed manufacturing apparatus may be controlled in accordance with the number. Further, at the confirmation of the suction, the confirmation can be carried out only when the suction solenoid is energized. During operation, the positions of the stepping motors are confirmed to eliminate mechanical trouble.

Figure 4:
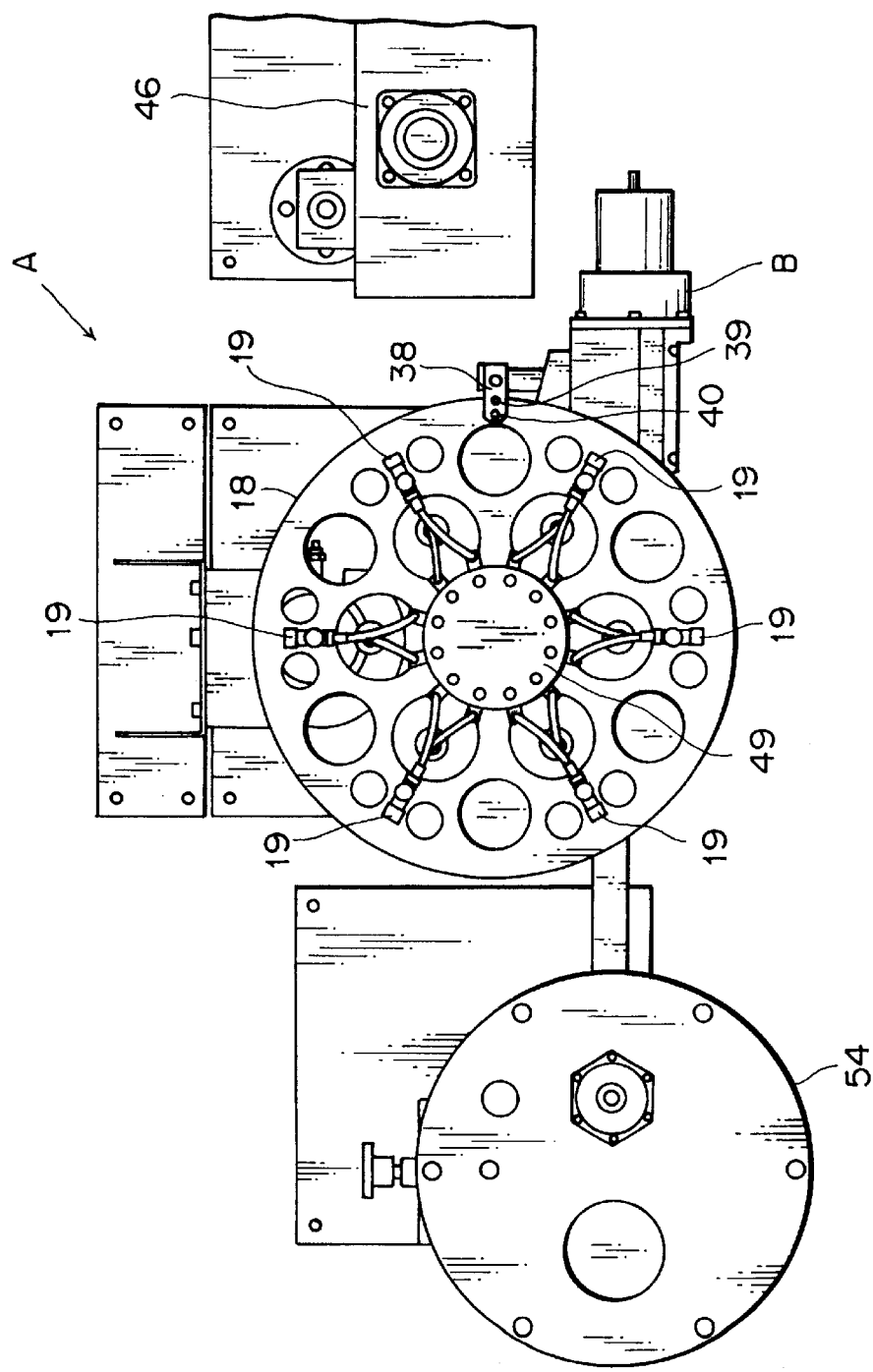
FIG. 4 is a plan view of the artificial seed manufacturing apparatus in FIG. 2.

Next, overall motions of the artificial seed manufacturing apparatus described above will be explained with reference FIGS. 2 to 4. The rotary plate 18 rotates together with the output shaft of the stepping motor 61, and the detection signal from the positioning sensor 39 causes the stepping motor 61 to stop, so that the tips 21 are positioned directly above the nozzle plunger 8 of the coating material delivery mechanism C and the supply rod 29 of the enclosure supply mechanism B.

Next, the tip air cylinder 19 is activated to lower the tip 21 and the supply rod air cylinder 31 of the enclosure supply mechanism B is operated to move the supply rod 29 upward, which causes a part of the enclosures immersed in the culture liquid in the enclosure container 25 to come close to the tip 21 with placed on the supply rod 29. As a result, the culture liquid with the enclosures on the supply rod 29 flows out of the supply rod 29 through the radially extending liquid discharge grooves 83.

A negative pressure is applied to the tip 21 approaching the enclosure, and then the tip air cylinder 19 is activated to move the tip 21 upward. The supply rod air cylinder 31 is activated to lower the supply rod 29 into the enclosure container 25. In parallel with this enclosure suction operation, the tip 21 that has drawn the enclosure and is positioned directly above the coating material delivery mechanism C is lowered by the operation of the tip air cylinder 19 so as to come close to the film of the coating material formed at the lower end of the nozzle plunger 8 of the coating material delivery mechanism C. Air pressure is supplied into the tip 21 to supply the enclosure onto the film of the coating material. After substantially simultaneous operation of suction and supply of the enclosure, the stepping motor 21 is again operated to rotate the rotary plate 18 by a required amount of angle, and the similar operation is repeated.

In the coating material delivery mechanism C, the stepping motor 61 of the drive unit C2 rotates alternately clockwise and counterclockwise by a specified angle given by the control unit 100. The pressure plunger 77 performs reciprocal motion over the length corresponding to this amount of rotation to move forward and backward the coating material in sol state in the coating material passage 9, thereby raising and lowering the pressure of the coating material in the passage 9. The pressure plunger 77 is activated over the length corresponding to this amount of rotation to alternately protrude and draw the coating material in the coating material passage 9 and to alternately increase and decrease the pressure of the coating material in the coating material passage, which in turn causes the nozzle plunger to open the valve, with the result that the coating material flows out from the nozzle plunger in an amount corresponding to the amount of operation of the pressure plunger. After this, the nozzle plunger closes the valve and then a film of the coating material forms at the lower end of the nozzle plunger. When the pressure of the coating material increases, the nozzle plunger 8 opens. When the pressure reduces, the coating material is supplied.

Therefore, the amount of the coating material delivered from the nozzle plunger 8 corresponds to the amount of rotation of the stepping motor 61, so that it is possible to easily adjust the amount of the coating material delivered without manual operation. When the nozzle plunger 8 closes the valve, the film of the coating material formed in the lower part of the nozzle plunger 8 droops by its own weight, and the enclosure is supplied from the tip 21. When the valve opens, the enclosure and air bubbles are enclosed by the coating material, and the enclosure with added weight falls into the hardener tank.

In order to increase the coat diameter, the stroke of the pressure plunger needs to be increased by specifying a greater amount of rotation for the stepping motor 61 from the control unit 100. When the number of enclosures is to be changed to two, the enclosure needs to be supplied twice for each valve opening. It is convenient since the enclosure container 25 and the supply rod 29 can easily be removed at the change of the kind of enclosure.

Detailed operation of the artificial seed manufacturing apparatus described above will be explained below with reference to the flow charts in FIGS. 23 to 33 showing the process controlled by the CPU 101 of the control unit 100 in accordance with a predetermined control programs, and the state transition diagrams in FIGS. 34 to 36.

Figure 23B:
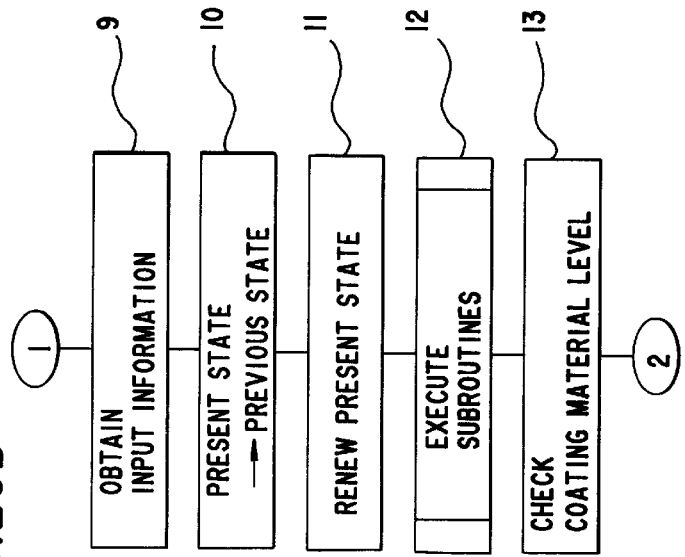
FIG. 23 is a main flowchart processed by a CPU in FIG. 14.
Figure 23A:
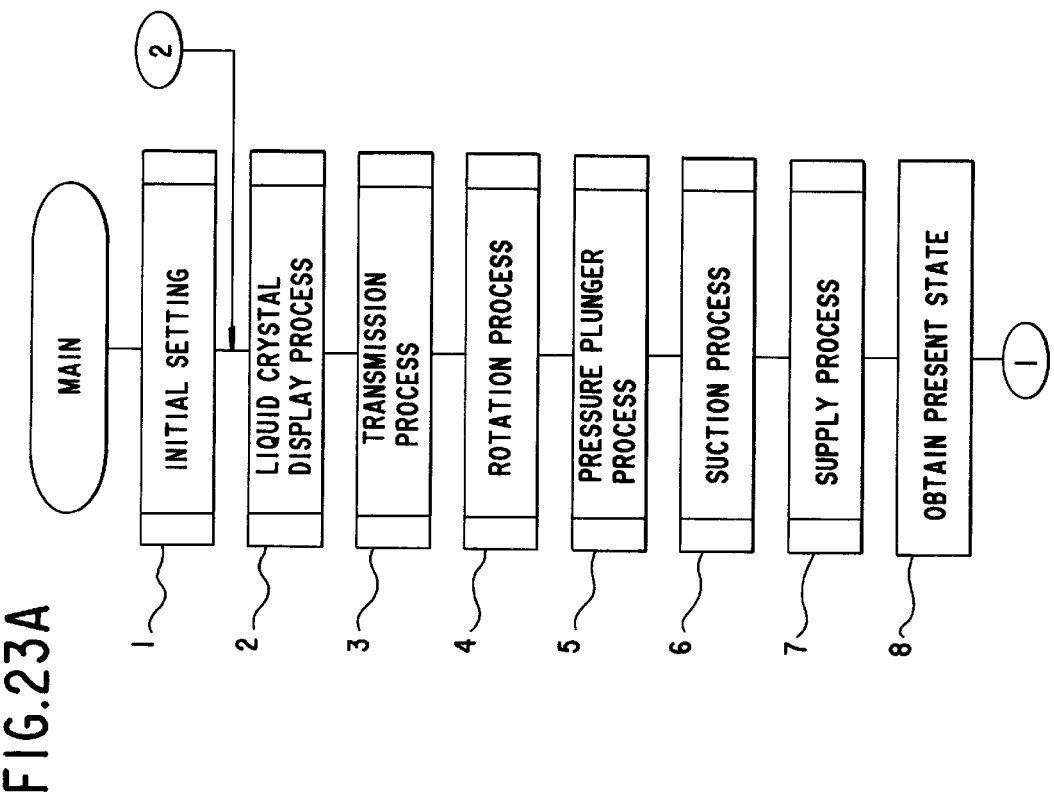

In a main routine shown in FIG. 23, the operation starts by switching ON a power source thereof, and at the first step S1, initial setting is performed. Then, the process advances to step S2 to carry out liquid crystal display process; at step S3 transmission process; at step S4 rotation process (see FIGS. 24 and 25); at step S5 pressure plunger process (see FIGS. 26 and 27); at step S6 suction process (see FIGS. 28 to 30); and at step S7 supply process (see FIGS. 31 to 33).

Then, the process advances to step S8 to obtain present state, and at step S9, input information is obtained. At the following step S10, previous state, which are stored in work area of the RAM 103, are replaced with the present state, and at step S11, state of the process are renewed based on the present state, which are obtained at step S8, and the input information which is obtained at step S9 with reference to the state transition diagrams in FIGS. 34 to 36. Then, at step S12, if subroutines are programmed, they are executed, and at step S13, the tank level of the coating material tank is checked through signals from the tank level sensors, and the process returns to step S2.

In the liquid crystal display process at step S2, the liquid crystal displayer 111 displays several data. For instance, when the manufacturing apparatus is operated manually, the liquid crystal displayer 111 displays as such. When the manufacturing apparatus is not operated manually, that is, in automatic operation mode, it is checked whether on not operation state are effectively set. If the operation state have not yet been set, the liquid crystal displayer 111 displays that parameters are ineffective. In such a case, that is, when the parameters are ineffective, the operation can not be started. When the parameters are effective, the liquid crystal displayer 111 displays that the apparatus can be operated in automatic operation mode. In this case, the liquid crystal displayer 111 displays the result and target of manufacturing as well as information regarding operation state and abnormality. Operation state displayed on the liquid crystal displayer 111 are stoppage, run, suspension, and abnormal trip. Information regarding abnormality on the liquid crystal displayer 111 relates to abnormality/no alarm, suction retry error, clogging of suction tip, abnormality in rotary stepping motor, abnormality in pressure plunger stepping motor, no coating material, abnormality in tip air cylinder, abnormality in supply rod air cylinder, and middle level of coating material.

In the transmission process at step S3, data are transmitted from the control unit 100 to the personal computer 112 in accordance with a command obtained through receive interruption not shown.

Prior to detailed explanation of each process described above, it will be explained how to read the state transition diagrams in FIGS. 34 to 36. When a start command is inputted from the personal computer during stoppage of the artificial seed manufacturing apparatus, the number of products is cleared; the solenoids are all deenergized; and the present state is set to rotary/pressure plunger origin reset start state. If abnormality is detected during the stoppage, all outputs are cleared to allow the state to be in abnormality. In this state, when a start command is inputted, the number of products is cleared; the solenoids are all deenergized; and the present state is set to rotary/pressure plunger origin reset start process. When a restart command is inputted in this state, the number of products is calculated again; the solenoids are all deenergized; and the present state is set to rotary/pressure plunger origin reset start process.

During the above-mentioned rotary/pressure plunger origin reset, the rotary and pressure plunger processes are carried out, which causes the present state to be converted to pressure plunger origin reset process through the rotary stop state, and to rotary origin reset process through the pressure plunger stop state. If completion signal is detected during the rotary/pressure plunger origin reset process, the rotary and pressure plunger processes are forced to be stopped to stop the artificial seed manufacturing apparatus. If abnormality is detected during the rotary/pressure plunger origin reset process, all outputs are cleared to allow the state to be in abnormality, and process similar to the above is carried out.

If rotary stop command is inputted during the rotary origin reset, the destination of the rotary plate 18 is set to be 120 degrees and the suction by the tip 21a starts. If interruption signal is inputted during the rotary origin reset process, the state moves to stoppage waiting rotary operation process to stop the artificial seed manufacturing apparatus by the rotary stop input signal. In this state, if a start signal is inputted, the number of products is cleared; the solenoids are all deenergized; and the state is set to the rotary/pressure plunger origin reset start process. When a restart signal is inputted in this state, the number of products as target is calculated again; the solenoids are all deenergized; and the state is set to the rotary/pressure plunger origin reset start process.

If pressure plunger stop command is inputted during the rotary origin reset process, the destination of the rotary plate 18 is set to be 120 degrees and the suction by the tip 21a starts. If an interruption signal is inputted during the rotary origin reset process, the present state is converted to stoppage waiting rotary operation to stop the artificial seed manufacturing apparatus by a rotary stop input signal. In this state, if a start signal is inputted, the number of products is cleared; the solenoids are all deenergized; and the state is set to the rotary/pressure plunger origin reset start process. When a restart signal is inputted in this state, the number of products as target is calculated again; the solenoids are all deenergized; and the state is set to the rotary/pressure plunger origin reset start process.

If a suction finish signal is inputted during suction process, the present state moves to rotation start process. When a tip at the completion of the suction is the tip 21c, the present state moves to initial positioning process. If a rotary stop signal is inputted during the rotary rotation process after the start of the rotation start process, the present state moves to suction start process. Then, the completion of the suction causes the tip to become the tip 21c, which permits the present state to be converted to initial positioning process.

When rotary stop command is inputted during the initial positioning process, the present state moves to suction start process and the tip 21c starts the suction. As a result, the present state moves to suction/supply process, and if a suction finish signal is inputted, the present state moves to rotation start process. In case that the number of enclosures to be enclosed is zero, the present state becomes completion waiting state. If a supply finish signal is inputted in the suction/supply state, the present state moves to suction process. Then, if the suction finish signal is inputted in the above-mentioned state, the present state moves to rotation start process.

The rotation start process converts the present state to rotary rotation state. When rotary stop signal is inputted in this state, the state moves to tact (time) waiting process. When a timer finish signal is inputted during the tact waiting process, the present state moves to suction start and supply start process, which converts the state to be suction/supply state, and the aforementioned motion is repeated until the number of products as target becomes zero. When the number of enclosures to be enclosed becomes zero, the present state moves to completion waiting process to stop the artificial seed manufacturing apparatus in accordance with the input of pressure plunger stop signal, which causes all motions to be stopped.

Next, the processes at steps S4 to S7 in the above-mentioned flow chart will be explained one after another in detail.

Figure 24:
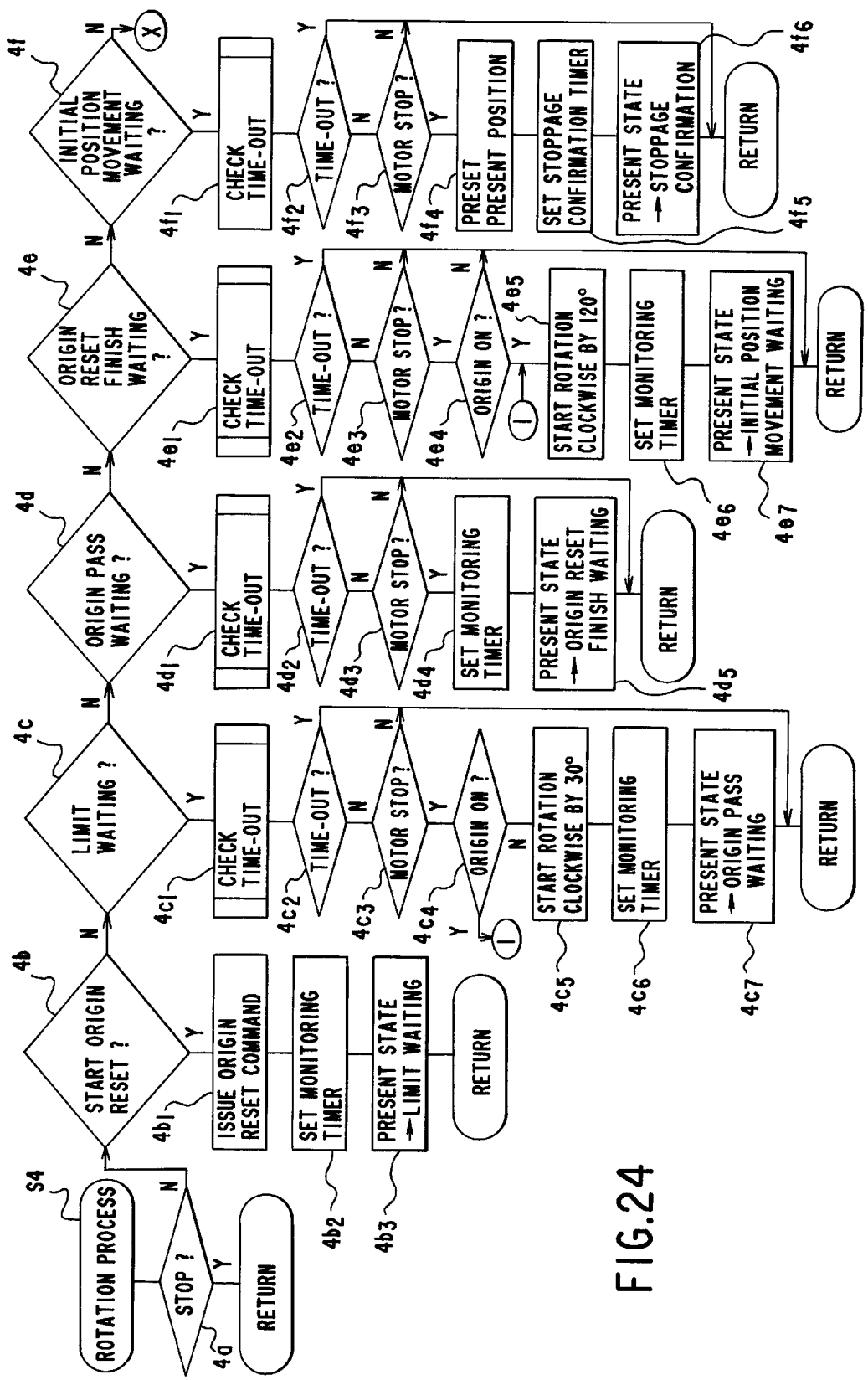
FIG. 24 is a detailed flowchart showing a part of rotation process in FIG. 23 in detail.
Figure 25:
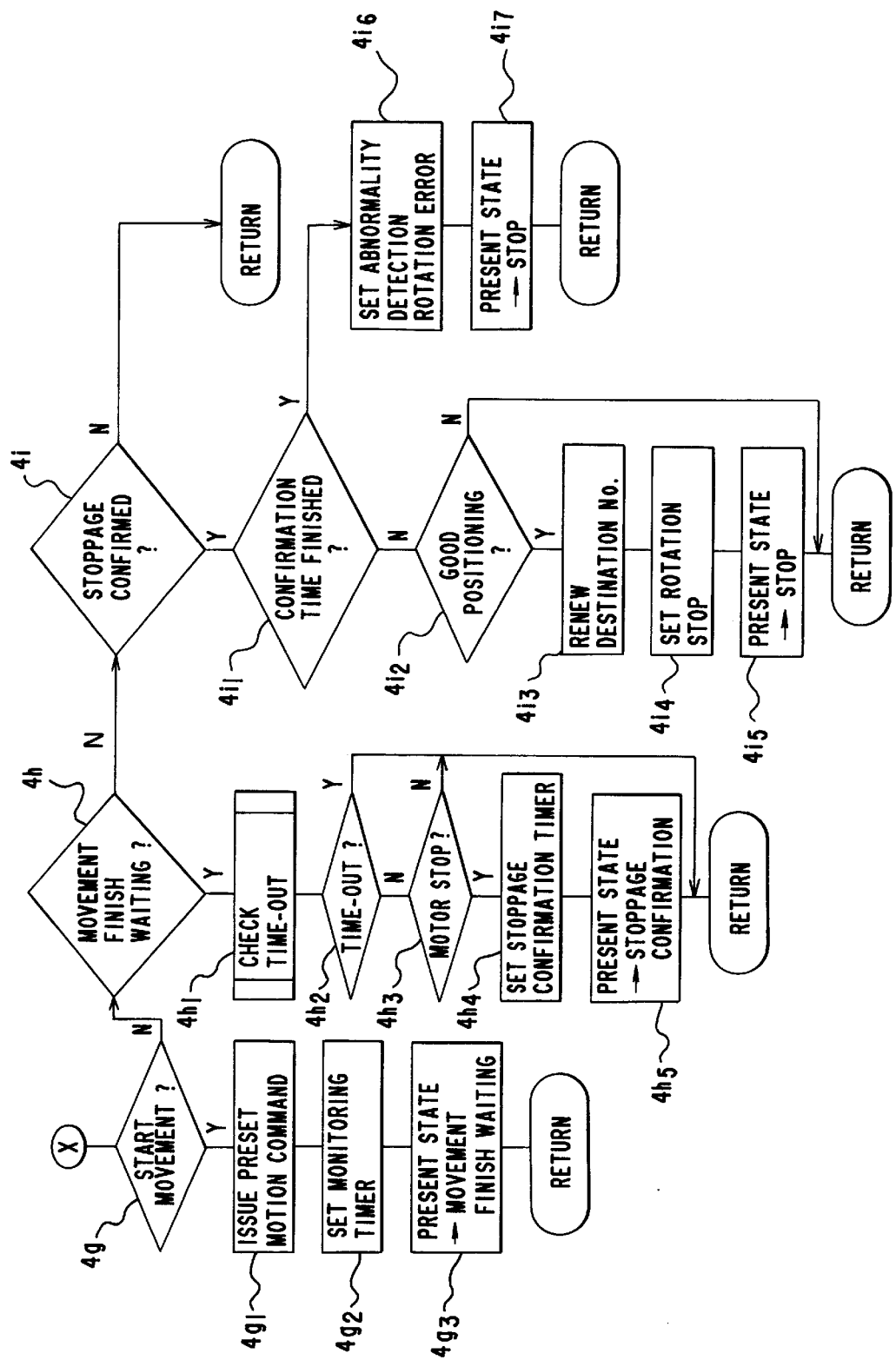
FIG. 25 is a flowchart showing another part of the rotation process in FIG. 23 in detail.

In the rotation process at step S4, as illustrated in FIG. 24, as first at step S4a, whether the artificial seed manufacturing apparatus stops or not is judged. If the result is YES, that is, if the artificial seed manufacturing apparatus stops, the process returns to the main routine in FIG. 23, and the process advances to step S5. When the artificial seed manufacturing apparatus is started by command from the personal computer 112 during the artificial seed manufacturing apparatus in not operated, and the present state is renewed with reference to the state transition diagram at step S11 so that the present state is converted from stop state to origin reset start process, the judgment at step S4a becomes NO, and the process advances to step S4b where it is judged whether the present state is in the origin reset start process or not. As a result, the judgment at step S4b becomes YES.

When the judgment at step S4b is YES, the present process advances to step S4b1 to issue the origin reset command designating the velocity and the number of steps of the rotary stepping motor and the like, and those data are outputted to the stepping motor controller 104. Then, the process advances to step S4b2 to set monitoring timer for restricting the operation time, and the process advances to step S4b3 to convert the present state from the origin reset start state to limit waiting state, and the process advances to step S5 in the main routine in FIG. 23. After the process advances to steps S4b3 to convert the present state to limit waiting state, when the process advances to step S4 of rotation process, the judgment at steps S4a and S4b becomes NO to cause the process to advance to step S4c, so that the judgment at this step becomes YES.

When the judgment at step S4c becomes YES, the process advances to step S4c1 to check the monitoring timer which is set at step S4b2, and whether time-out occurs or not is judged at the following step S4c2. If the judgment is NO at step S4c2, that is, if time-out does not occur, the process advances to step S4c3 where whether or not the rotary stepping motor rotates and stops in accordance with the step number, which is set at step S4b1 through a signal from the stepping motor controller 104. If the judgment at step S4c3 is NO, the process advances to step S5 in the main routine in FIG. 23 to repeat the aforementioned procedure, on the other hand, if the judgment at step S4c3 is YES, the process advances to step S4c4 to judge whether or not the original position sensor turns ON. If the result at this step is YES, the process advances to step S4e4 described below, and if the result is NO, the process advances to step S4c5.

At step S4c5, the stepping motor controller 104 causes the rotary stepping motor to rotate clockwise by 30 degrees, and then the process advances to step S4c6 to set the monitoring timer for restricting operation time, and to step S4c7 to convert the present state from the limit waiting state to origin pass waiting state. And then, the process advances to step S5 in the main routine in FIG. 23. After the present stated is converted into the origin pass waiting state at step S4c7, when the process enters the rotation process at step S4, the judgment at steps S4a to S4c become NO to cause the process to advance step S4d, and the judgment at this step becomes YES.

When the judgment at step S4*d* becomes YES, the process advances to step S4*d*1 to check the monitoring timer, which is set at step S4*c*6, to judge at the following step S4*d*2 whether or not time-out occurs. If the judgment at step S4*d*2 is NO, that is, if time-out does not occur, the process advances to step S4*d*3 to judge whether or not the rotary stepping motor rotates and stops in accordance with the step number for 30 degrees, which starts at step S4*c*5, through a signal from the stepping motor controller 104. If the judgment at step S4*d*3 is NO, the process advances to step S5 in the main routine in FIG. 23 to repeat the above-mentioned procedure. If the judgment at step S4*d*3 is YES, the process advances to step S4*d*4 to set monitoring timer for restricting the operation time, and the process advances to step S4*d*5 to convert the present state from the origin pass waiting state to origin reset waiting state, and then, the process advances to step S5 in FIG. 23. When the present state is converted to the origin reset waiting state, when the process enters the rotation process at steps S4*a* to S4*d*, the judgment at steps S4*a* to S4*d* become NO, so that the process advances to step S4*e* and the judgment at this step becomes YES.

When the judgment at step S4 becomes YES, the process advances to step S4*e*1 to check the monitoring timer, which is set at step S4*d*4, to judge at the following step S4*e*2 whether or not time-out occurs. If the judgment at step S4*e*2 is NO, that is, if time-out does not occur, the process advances to step S4*e*3 to judge whether or not the rotary stepping motor rotates and stops through a signal from the stepping motor controller 104. If the judgment at step S4*e*3 is NO, the process advances to step S5 in the main routine in FIG. 23 to repeat the above-mentioned procedure. If the judgment at step S4*e*3 is YES, the process advances to step S4*e*4 to judge whether or not the original position sensor turns ON. If the judgment at this step is YES, the process advances to step S4*e*5. If the judgment is NO, the process advances to step S5 in the main routine in FIG. 23.

At step S4*e*5, the stepping motor controller 104 causes the rotary stepping motor to rotate clockwise by 120 degrees, and the process advances to step S4*e*6 to set the monitoring timer for restricting the operation time, then the process advances to step S4*e*7 to convert the present state from the origin reset waiting state to initial position movement waiting state, and the process advances to step S5 in the main routine in FIG. 23. At the step S4*e*7, after the present state is converted into the initial position movement waiting state, when the process enters the rotation process at step S4, the judgment at steps S4*a* to S4*e* become NO and the process advances to step S4*f* to allow the judgment at this step to turn YES.

When the judgment at step S4*f* becomes YES, the process advances to step S4*f*1 to check the monitoring timer, which is set at step S4*e*6, and to judge whether or not time-out occurs at step S4*f*2. If the judgment at step S4*f*2 is NO, that is, if time-out does not occur, the process advances to step S4*e*3 to judge whether or not the rotary stepping motor rotates and stops in accordance with the step number of 120 degrees, which is started at step S4*e*5, through a signal from the stepping motor controller 104. The motor controller is set pulse number for 120 degrees in a counter thereof and judges the stoppage of the motor when the number is decreased into zero. If the judgment at step S4*f*3 is NO, the process advances to step S5 in the main routine in FIG. 23 to repeat the above-mentioned procedure. If the judgment at step S4*f*3 is YES, the process advances to step S4*f*4 to preset the present position by setting a bit of initial position state. Then, the process advances to step S4*f*5 to set the monitoring time for confirming the stoppage, and the process advances to step S4*f*6 to convert the present state from the initial position movement waiting state to stoppage confirming state, and the process advances to step S5 in the main routine in FIG. 23. After the present state is converted to the stoppage confirming state at step S4*f*6, and when the process enters the rotation process at step S4, the judgment at steps S4*a* to S4*h* in FIGS. 24 and 25 become NO, and the process advances to step S4*i* to allow the judgment at this step to turn YES.

When the judgment at step S4*i* turns YES, the process advances to step S4*i* and checks the stoppage confirmation timer, which is set at step S4*f*5, to judge whether the confirmation time is finished or not. If the judgment at step S4*i*1 is NO, that is, if within the confirmation time, the process advances to step S4*i*2 to judge whether or not the rotary plate 18 stops at a predetermined position by monitoring signals from the sensor. If the judgment at step S4*i*2 is NO, the process advances to step S5 in the main routine in FIG. 23. If the judgment is YES, the process advances to step S4*i*3 to renew the number of destination by setting the step number for rotating the rotary stepping motor to move the rotary plate 18 to the next destination to the pulse counter. Further, in step S4*i*4, after the rotary stoppage is selected, the process advances to step S4*i*5 to convert the present state from the stoppage confirmation state to the stop state, and the process advances to step S5 in the main routine in FIG. 23.

If the judgment at step S4*i*1 is YES, that is, if the stoppage of the rotary plate 18 at the predetermined position is not judged at step S4*i*2 after the confirmation time passes, the process advances to step S4*i*6 to set abnormality detection, and the process advances to step S4*i*7 to convert the present state from the stoppage confirmation state to stop state, and the process advances to step S5 in the main routine in FIG. 23. If the judgment at step S4*i* is also NO, the process advances to step S5 in the main routine in FIG. 23.

When the present state is in rotation start process, the judgment at step S4*g* becomes YES, so that the process advances to step S4*g*1, and preset motion command which designates rotation step number and the like of the rotary stepping motor, which is required for rotating the rotary plate 18 to the destination, is issued and is outputted to the stepping motor controller 104. Then, the process advances to step S4*g*2 to set the monitoring timer for restricting the operation time, and the process advances to step S4*g*3 to convert the present state from the stop state to movement finish waiting state, and the process advances to step S5 in the main routine in FIG. 23. After the present state is converted from the stop state to the movement finish waiting state, when the process enters the rotation process at step S4*g*3, the judgment at steps S4*a* to S4*g* turn NO, and the process advances to step S4*h* to cause the judgment at this step to turn YES.

When the judgment at step S4*h* turns YES, the process advances to step S4*hi* and checks the monitoring timer, which is set at step S4*g*3, to judge whether the monitoring time is finished or not. If the judgment at step S4*h*2 is NO, that is, if within the monitoring time, the process advances to step S4*h*3 to judge whether or not the rotary stepping motor rotates in accordance with the step number, which is designated at step S4*g*1, and then stops through signals from the stepping motor controller 104. If the judgment at step S4*h*3 is NO, the process advances to step S5 in the main routine in FIG. 23. If the judgment is YES, the process advances to step S4*h*4 to set monitoring timer for restricting the time for confirming the stoppage, and the process advances to step S4*h*5 to convert the present state from movement finish waiting state to the stoppage confirmation state, and the process advances to step S5 in the main routine in FIG. 23. After the present state is converted to the stoppage confirmation state at step S4h5, when the process enters the rotation process at step S4, the judgment at steps S4a to S4h become NO to allow the process to advance to step S4i, and the processes after this step are performed to convert the present state to stop state again, and the process advances to step S5 in the main routine in FIG. 23.

Figure 26:
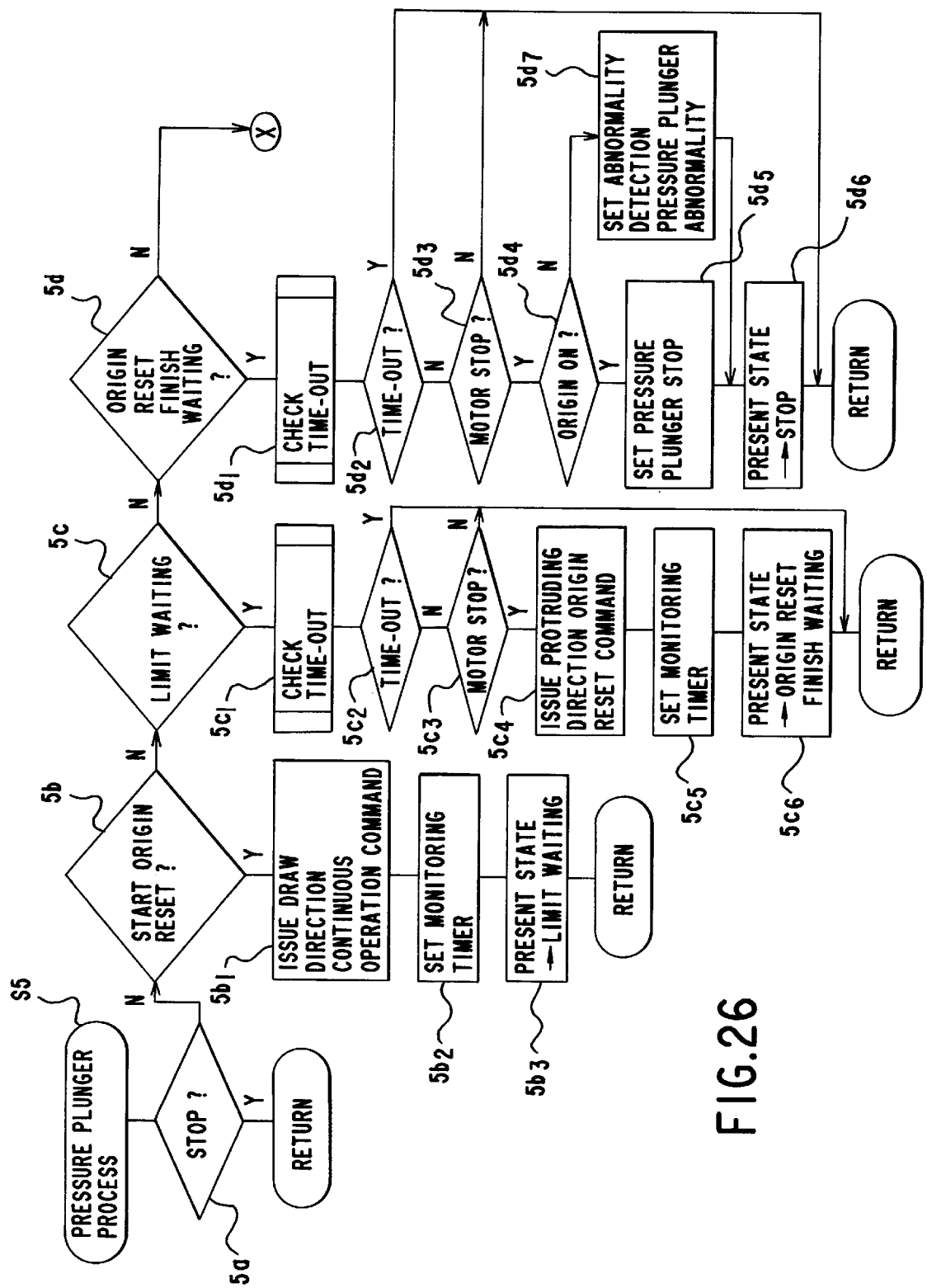
FIG. 26 is a flowchart showing a part of the pressure plunger process in FIG. 23 in detail.

In the pressure plunger process at step S5, as illustrate in FIG. 26, at first, whether the present state is in stop state or not is judged at step S5a, and if the judgment is YES, the process returns to the main routine in FIG. 23, and the process advances to step S6. When the artificial seed manufacturing apparatus is in stop state; a command from the personal computer 112 starts the artificial seed manufacturing apparatus; the present state is renewed with reference to the state transition diagrams at step S11; and the present state is converted from stop state to origin reset start state, the judgment at step S5a becomes NO and the process advances to step S5b where it is judged whether or not the present state is in the origin reset start state, and the judgment at this step becomes YES.

When the judgment at step S5b is YES, the process advances to step S5b1, and draw continuous command designating the velocity, the step number, and the like of the pressure plunger stepping motor in a direction that the pressure plunger is drawn is issued and is outputted to the stepping motor controller 104. Then, the process advances to step S5b2 to set the monitoring timer for restricting the operation time, and the process advances to step S5b3 to convert the present state from origin reset start state to limit waiting state, and the process advances to step S5 in the main routine in FIG. 23. After the present state is converted to the limit waiting state, when the process enters the pressure plunger process at step S5, the judgment at steps S5a and S5b turn NO, and the process advances to step S5c to cause the judgment at this step to turn YES.

When the judgment at step S5c becomes YES, the process advances to step S5c1 to check the monitoring timer, which is set at step S5b2, to judge at the following step S5c2 whether or not time-out occurs. If the judgment at step S5c2 is NO, that is, if time-out does not occur, the process advances to step S5c3 to judge whether or not the pressure plunger stepping motor rotates and stops in accordance with the step number, which is set at step S5b1, through a signal from the stepping motor controller 104. If the judgment at step S5c3 is NO, the process advances to step S6 in the main routine in FIG. 23 to repeat the above-mentioned procedure. If the judgment at step S5c3 is YES, the process advances to step S5c4 to set protruding direction origin reset command designating the step number and the like of the pressure plunger stepping motor in a direction that the pressure plunger returns to the origin is issued and is outputted to the stepping motor controller 104, and the process advances to step S5c5 to set monitoring timer for restricting the operation time, and the process advances to step S5c6 to convert the present state from the limit waiting state to origin reset waiting state, and then, the process advances to step S6 in the main routine in FIG. 23. After the present state is converted into the origin reset waiting state at step S5c6, when the process enters the pressure plunger process at steps S5, the judgment at steps S5a to S5c become NO, so that the process advances to step S5d and the judgment at this step becomes YES.

When the judgment at step S5d becomes YES, the process advances to step S5d1 to check the monitoring timer, which is set at step S5c5, to judge at the following step S5d2 whether or not time-out occurs. If the judgment at step S5d2 is NO, that is, if time-out does not occur, the process advances to step S5d3 to judge whether or not the pressure plunger stepping motor rotates and stops in accordance with the predetermined step number, which is designated by the protruding direction origin reset command at step S5c4, through a signal from the stepping motor controller 104. If the judgment at step S5d3 is NO, the process advances to step S6 in the main routine in FIG. 23 to repeat the above-mentioned procedure. If the judgment at step S5d3 is YES, the process advances to step S5d4 to judge whether or not the origin positioning sensor turns ON. If the judgment is YES, the process advances to step S5d5 to set the pressure plunger stoppage, and the process advances to step S5c6 to convert the present state from the origin reset finish state to stop state, and the process advances to step S6 in the main routine in FIG. 23. If the judgment at step S5d4 is NO, the process advances to step S5d7 to set abnormality detection and to output the pressure plunger abnormality, and the process advances to step S5d6 to set stoppage.

Figure 27:
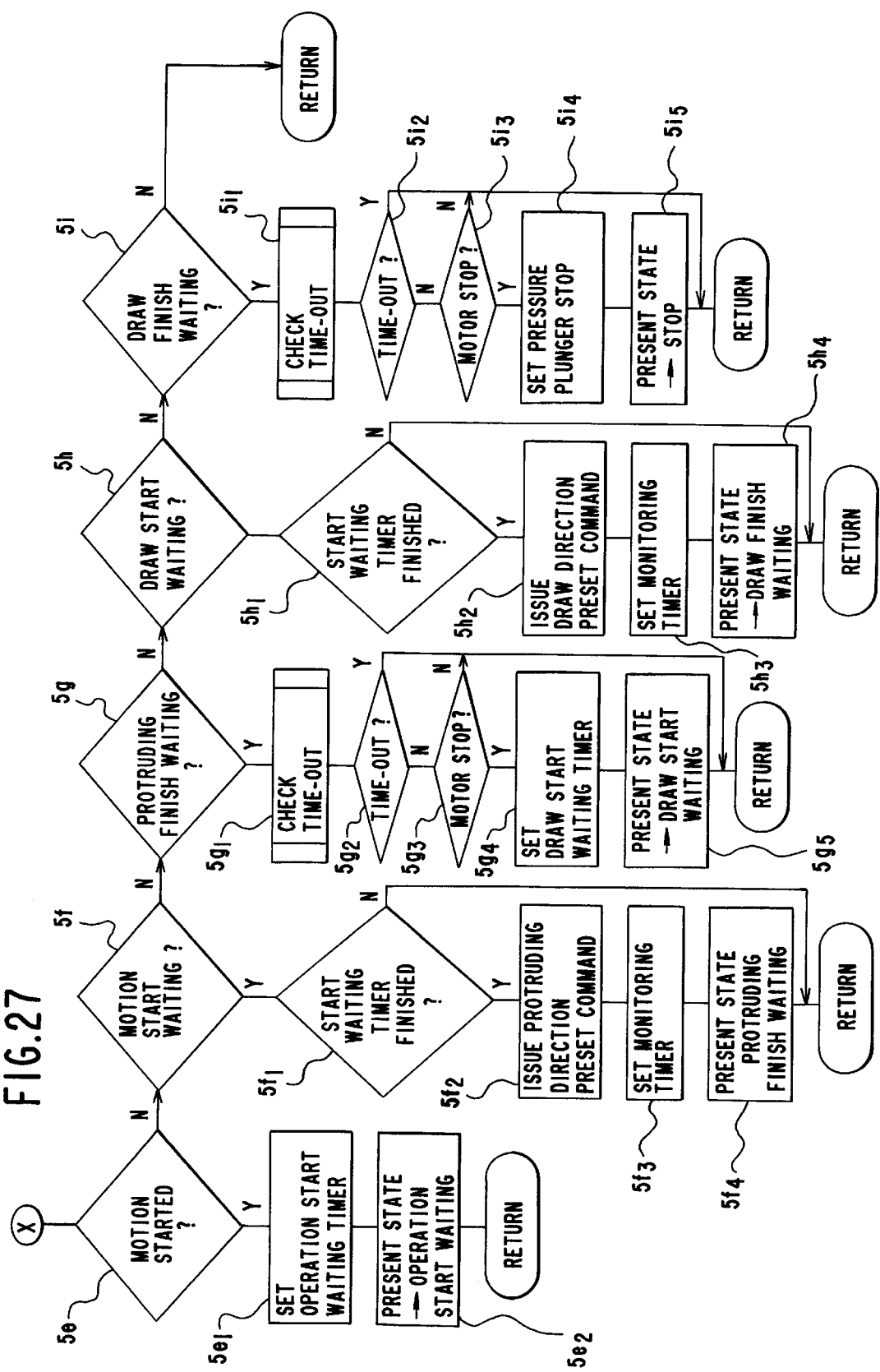
FIG. 27 is a flowchart showing another part of the pressure plunger process in FIG. 23 in detail.

When the present state is in the pressure plunger motion start state, the judgment at steps S5a to S5d become NO, and the process advances to step S5e1 in FIG. 27, and then the judgment at step S5e becomes YES, and the process advances to step S5e1. After a timer for restricting the time for waiting the start of the motion at step S5e1, the process advances to step S5e2 where the present state is converted from the stop state to motion start waiting state, and the process advances to step S6 in the main routine in FIG. 23. After the present state is converted into the motion start waiting state at step S5e2 and the process enters the pressure plunger process at step S5, the judgment at steps S5a to S5e become NO, and the process advances to step S5f to allow the judgment at this step to turn YES.

When the judgment at step S5f becomes YES, the process advances to step S5f1 to check the monitoring timer, which is set at step S5e1, to judge whether or not time-out occurs. If the judgment at step S5f1 becomes YES, the process advances to step S5f2. At step S5f2, a protruding direction preset command for designating step number and the like for the rotation of the pressure plunger stepping motor, which is required to protrude a predetermined amount of coating material, is issued and is outputted to the stepping motor controller 104. Then, the process advances to step S5f3 to set monitoring timer for restricting the operation time, and the process advances to step S5f4 to convert the present state from motion start waiting state to protruding finish waiting state, and the process advances to step S6 in the main routine in FIG. 23. After the present state is converted into the protruding finish waiting state at step S5f4, when the process enters the pressure plunger process at step S5, the judgment at steps S5a to S5f turn NO, and the process advances to step S5g to cause the judgment at this step to become YES.

When the judgment at step S5g becomes YES, the process advances to step S5g1 to check the monitoring timer, which is set at step S5f3, and to judge at step S5g2 whether or not time-out occurs. If the judgment advances step S5g2 is NO, that is, if the time-out does not occur, the process advances to step S5g3 to judge whether or not the pressure plunger stepping motor rotates and stops in accordance with the step number which is set at step S5c4 through a signal from the stepping motor controller 104. If the judgment at step S5g3 is NO, the process advances to step S6 in the main routine in FIG. 23 to repeat the above-mentioned procedure. If the judgment at step S5g3 is YES, the process advances to step S5g4 to set time for restricting time required to wait the start of draw, and the process advances to step S5g4 to convert the present state from the protrusion waiting state to draw start waiting state, and the process advances to step S6 in the main routine in FIG. 23. After the present state is converted into the draw start waiting state at step S5g5, when the process enters the pressure plunger process at step S5, the judgment at steps S5a to S5g become NO, so that the process advances to step S5h to cause the judgment at this step to become YES.

If the judgment at step S5h becomes YES, the process advances to step S5h1 to judge whether or not the draw start waiting time, which is set at step S5g4, is finished or not. If the judgment at step S5h1 becomes YES, the process advances to step S5h2. At step S5h2, draw direction present command for designating step number in the direction that the pressure plunger is drawn and the like of the pressure plunger stepping motor is issued and is outputted to the stepping motor controller 104. Then, the process advances to step S5h3 to set the monitoring time for restricting the operation time, and the process advances to step S5h4 to convert the present state from the draw start waiting state to draw finish waiting state, and the process advances to step S6 in the main routine in FIG. 23. After the present state is converted into the pressure plunger process at step S5h4, when the process enters the pressure plunger process at step S5, the judgment at steps S5a to S5h become NO, and the process advances to step S5i to cause the judgment at this step to become YES.

When the judgment at step S5i becomes YES, the process advances to step S5h3 to check the monitoring timer, which is set at step S5h3, and to judge at step S5i2 whether or not time-out occurs. If the judgment advances step S5i2 is NO, that is, if the time-out does not occur, the process advances to step S5i3 to judge whether or not the pressure plunger stepping motor rotates and stops in accordance with the step number which is set at step S5h2 through a signal from the stepping motor controller 104. If the judgment at step S5i3 is NO, the process advances to step S6 in the main routine in FIG. 23 to repeat the above-mentioned procedure. If the judgment at step S5i3 is YES, the process advances to step S5i4 to set time for restricting time required to wait the start of draw, and the process advances to step S5i5 to convert the present state from the draw finishing waiting state to stop state, and the process advances to step S6 in the main routine in FIG. 23. If the judgment at step S5i is NO, the process immediately advances to step S6 in the main routine in FIG. 23.

Figure 28:
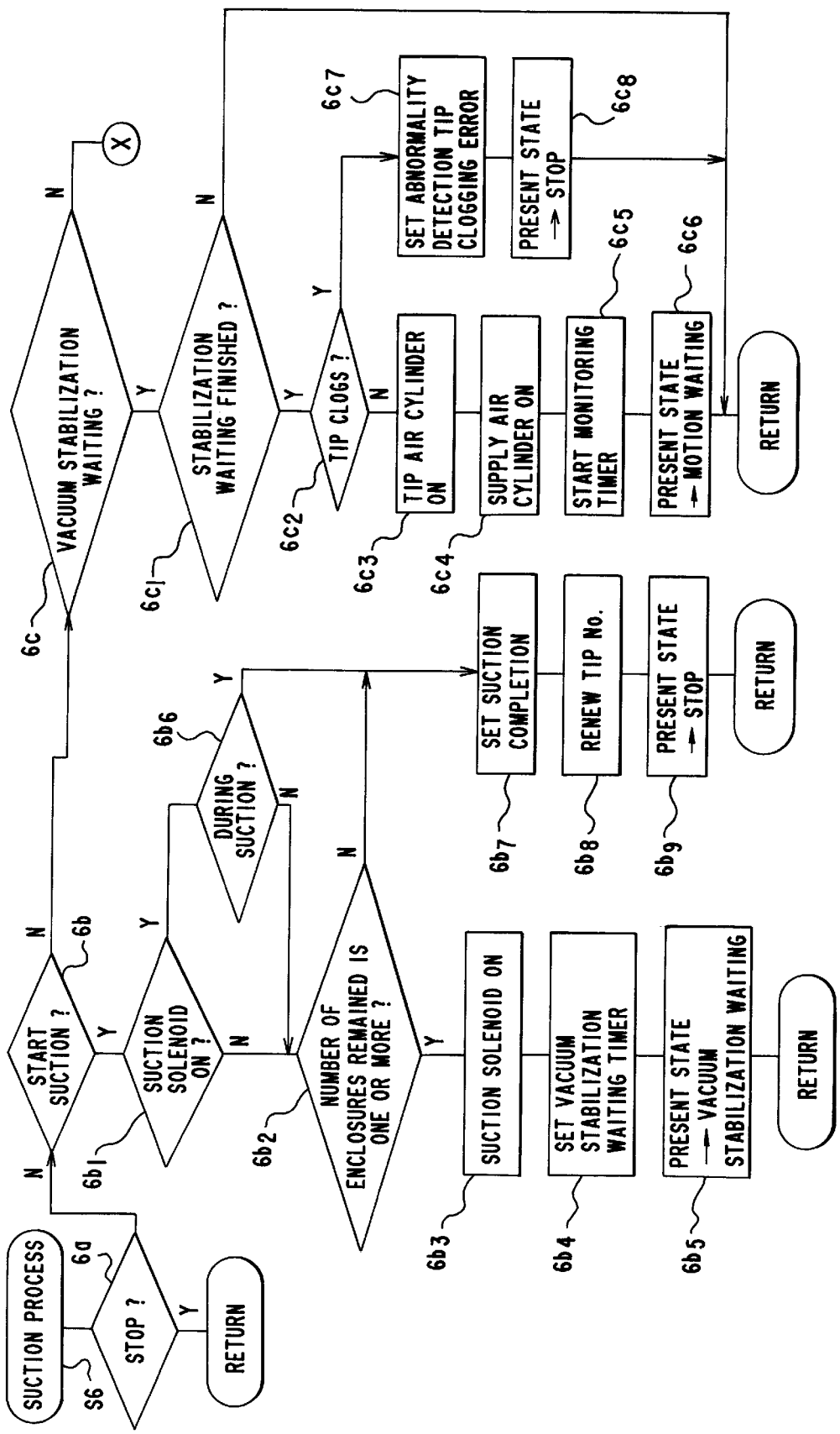
FIG. 28 is a flowchart showing a part of the suction process in FIG. 23 in detail.

In the suction process at step S6, as shown in FIG. 28, at first, whether the present state is in stop state or not is judged at step S6a, and if the judgment is YES, the process returns to the main routine in FIG. 23, and the process advances to step S7. Then, as illustrated in the state transition diagram in FIG. 34, when the present state is in rotary origin reset state, in rotary state, or initial positioning state, and the rotary stop state is selected or when the present state is in pressure plunger origin reset state and pressure plunger stoppage is selected, the present state is renewed in accordance with the state transition diagram at step S11, and the present state becomes suction start state. In this suction start state, the judgment at step S6a becomes NO, and the process advances to step S6b to judge whether or not the present state is suction start state, and the judgment at this step S6b becomes YES.

If the judgment at step S6b is YES, the process advances to step S6b1 to judge whether or not the suction solenoid is energized. When the judgment is NO, that is, if the solenoid is not energized, the process advances to step S6b2 to judge whether or not the number of enclosures remained is one or more, that is, whether or not the number of target is larger than that of products. The step S6b2 is carried out to eliminate enclosure under suction process when the process is finished. If the judgment at step S6b2 is YES, that is, if the number of products do not reach the number of target, the process advances to step S6b3 to energize the suction solenoid, and the process advances to step S6b4 to set timer for vacuum stabilization waiting timer, and the process advances to step S6b5 to convert the present state to the vacuum stabilization waiting state, and the process advances to step S7 in the main routine in FIG. 23.

When the judgment at step S6b1 is YES, that is, if the suction solenoid has already been energized at the suction start state, the process advances to step S6b6 to judge whether or not the tip has sucked an enclosure as suction finishing process at restart. If the judgment at step S6b6 is NO, the process advances to step S6b2. If the judgment at step S6b6 is YES, the process advances to step S6b7. At step S6b7, the suction completion is set, and the process advances to step S6b8 to renew tip number, and the process advances to step S6b9 to convert the present state from the suction start state to stop state, and the process advances to step S7 in the main routine in FIG. 23. When the judgment at step S6b2 is NO, that is, if the number of products reaches the number of target, the process advances to step S6b7 without sucking new enclosure to eliminate enclosure during suction process.

After the present state is converted into the vacuum stabilization waiting state at step S6b5, when the process enters the suction process at step S6, the judgment at steps S6a to S6b become NO, and the process advances to step S6c and the judgment at this step becomes YES. When the judgment at step S6c becomes YES, the process advances to step S6c1 to check timer which is set at step S6b4 and to judge whether or not the stabilization waiting process is completed. If the judgment at step S6c1 is YES, the process advances to step S6c2 to judge whether or not the tip clogs. When the tip does not clog and the judgment at step S6c2 is NO, the process advances to step S6c3 to energize the tip rod air cylinder. Then, the process advances to step S6c4 to energize the supply air cylinder. Then, at step S6c5, the monitoring time for restricting the operation time is set, and the process advances to step S6c6 to convert the present state from the vacuum stabilization waiting state to the motion waiting state, and the process advances to step S7 in the main routine in FIG. 23.

If the judgment at step S6c2 is YES, the process advances to step S6c7 to set abnormality detection to output tip clogging error, and at step S6c8, the present state, which is converted into vacuum stabilization waiting state at step S6b5, is converted into stop state, and the process advances to step S7 in the main routine in the FIG. 23.

Figure 29:
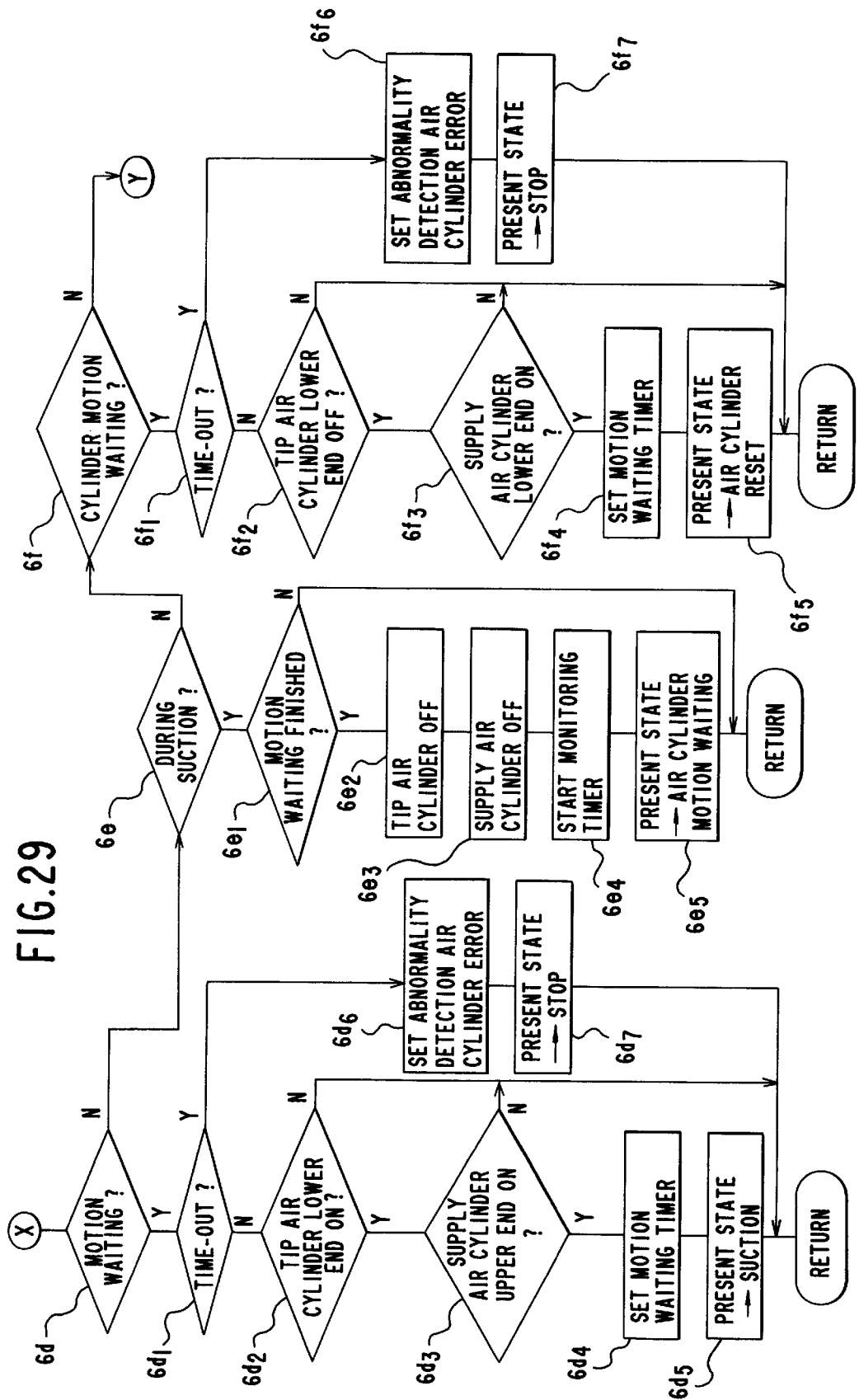
FIG. 29 is a flowchart showing another part of the suction process in FIG. 23 in detail.

After the present state is converted to motion waiting state at step S6c6, when the process enters the suction process at step S6, the judgment at steps S6a to S6c become NO, and the process advances to step S6d in FIG. 29, and the judgment at this step becomes YES. When the judgment at step S6d becomes YES, the process advances to step S6d1 to judge whether or not the time-out of the monitoring timer occurs. If the judgment at step S6d1 is NO, the process advances to step S6d2 to judge the lower end position detecting sensor of the tip air cylinder is energized. If the judgment at step S6d2 is YES, the process advances to step S6d3 to judge whether or not the upper end position sensor of the supply rod is energized. If the judgment step S6d3 is also YES, the process advances to step S6d4 to set the motion waiting timer, and the process advances to step S6d5 to convert the present state from the motion waiting state to suction process, and the process advances to step S7 in the main routine in FIG. 23.

When the judgment at step S6d1 is YES, the process advances to step S6d6 to set abnormality detection and to output air cylinder error, and at step S6d7, the present state, which is converted into motion waiting state at step S6b5, is converted into stop state, and the process advances to step S7 in the main routine in FIG. 23.

After the present state is converted into the suction state at step S6d5, when the process enters the suction process at step S6, the judgment at steps S6a to S6d become NO, and the process advances to step S6e to cause the judgment at this step to turn YES. When the judgment at step S6e becomes YES, the process advances to step S6e1 to judge whether or not the motion waiting time, which is set at step S6d4, is finished. If the judgment at step S6e1 is YES, the process advances to step S6e2 to deenergize the tip air cylinder, and the process advances to step S6e3 to deenergize the supply rod air cylinder. Then, the process advances to step S6e4 to set the monitoring timer for restricting the operation time, and the process advances to step S6e5 to convert the present state from the suction state to air cylinder motion waiting state, and the process advances to step S7 in the main routine in FIG. 23.

Figure 30:
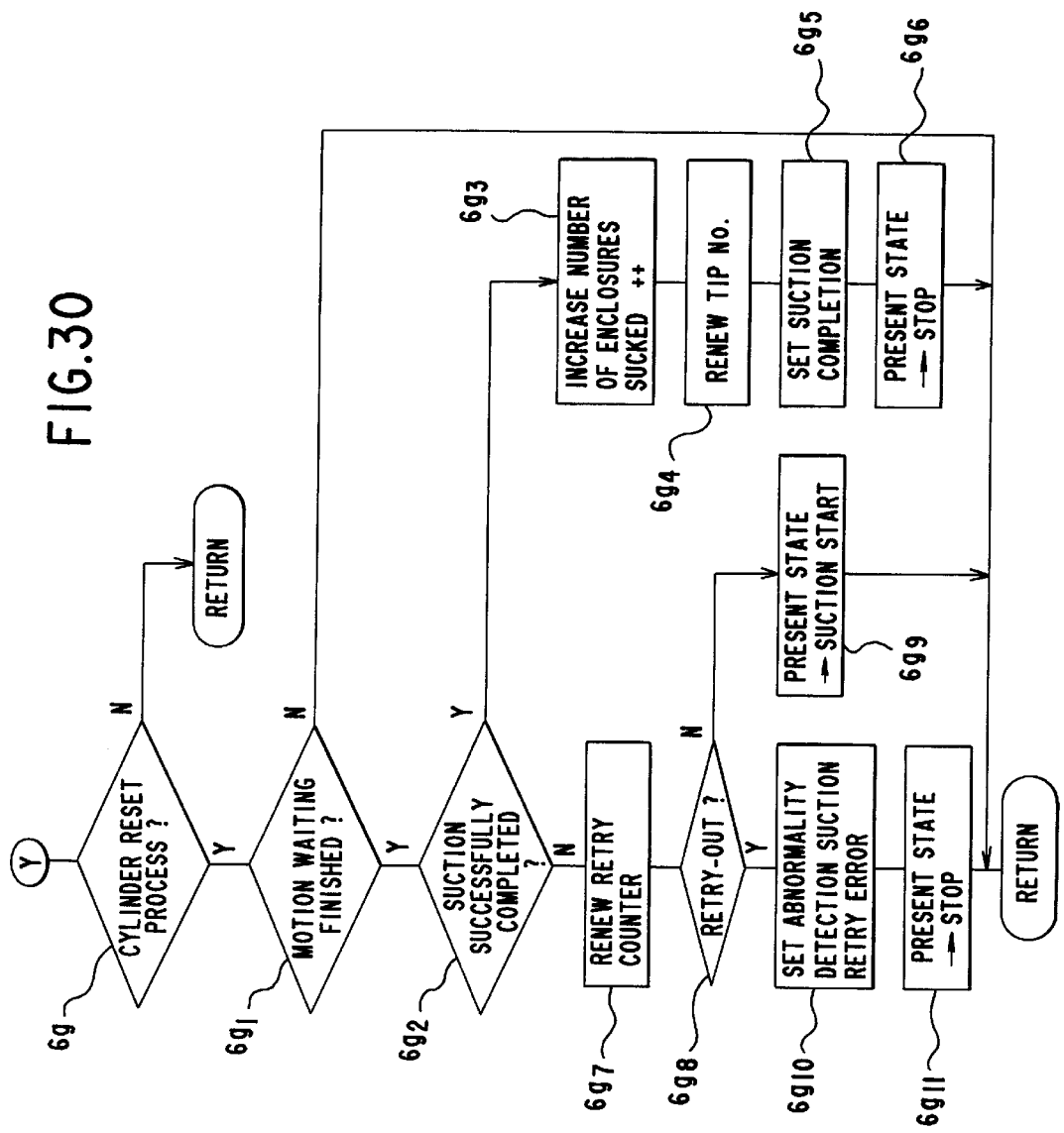
FIG. 30 is a flowchart showing a further part of the suction process in FIG. 23 in detail.

As described above, after the present state is converted into the air cylinder motion waiting state at step S6e5, when the process enters the suction process at step S6, the judgment at steps S6a to S6e become NO, and the process advances to step S6f in FIG. 30 to cause the judgment at this step to turn YES. When the judgment at step S6f becomes YES, the process advances to step S6f1 to judge whether on not the monitoring timer, which is set at step S6e4, causes time-out. If the judgment at step S6f1 is NO, the process advances to step S6f2 to judge whether or not the lower position detecting sensor of the tip air cylinder turns OFF, and if the judgment at step S6f2 is YES, the process advances to step S6f3 to judge whether or not the lower position detecting sensor of the supply rod air cylinder turns ON. If the judgment at step S6f3 is also YES, the process advances to step S6f4 to set motion waiting timer, and the process advances to step S6f5 to convert the present state from air cylinder motion waiting process to air cylinder reset process, and the process advances to step S7 in the main routine in FIG. 23.

When the judgment at step S6f1 is YES, the process advances to step S6f6 to set abnormality detection and to output the cylinder error, and at step S6f7, the present state, which is converted into the air cylinder motion waiting state at step S6e5, is converted into stop state, and the process advances to step S7 in the main routine in FIG. 23.

As described above, after the present state is converted into the air cylinder return state at step S6f5, when the process enters the suction process at step S6, the judgment at steps S6a to S6f become NO, and the process advances to step S6g to cause the judgment at this step to turn YES. When the judgment at step S6g becomes YES, the process advances to step S6g1 to judge whether on not the monitoring timer, which is set at step S6f4, causes time-out. If the judgment at step S6f1 is YES, the process advances to step S6g2 to judge whether or not the suction operation is successfully completed. If the judgment at step S6g2 is YES, the process advances to step S6g3 to increase the number of the enclosures sucked. Then, the process advances to step S6g4 to renew the number of the tip to 1, 2, 3, 6, 5, 4 in this order, and the process advances to step S6g5 to set the suction completion. Then, the process advances to step S6g6 to convert the present state from the air cylinder return state to stop state, and the process advances to step S7 in the main routine in the FIG. 23.

When the judgment at step S6g2 is NO, the process advances to step S6g7 to renew the retry counter, and then the process advances to step Sg8 to judge whether or not the number of retries is exceeded to cause retry-out. If the judgment at step S6g8 is NO, the process advances to step S6g9 to convert the present state from the air cylinder return state to suction start state, and the process advances to step S7 in the main routine in the FIG. 23.

Figure 31:
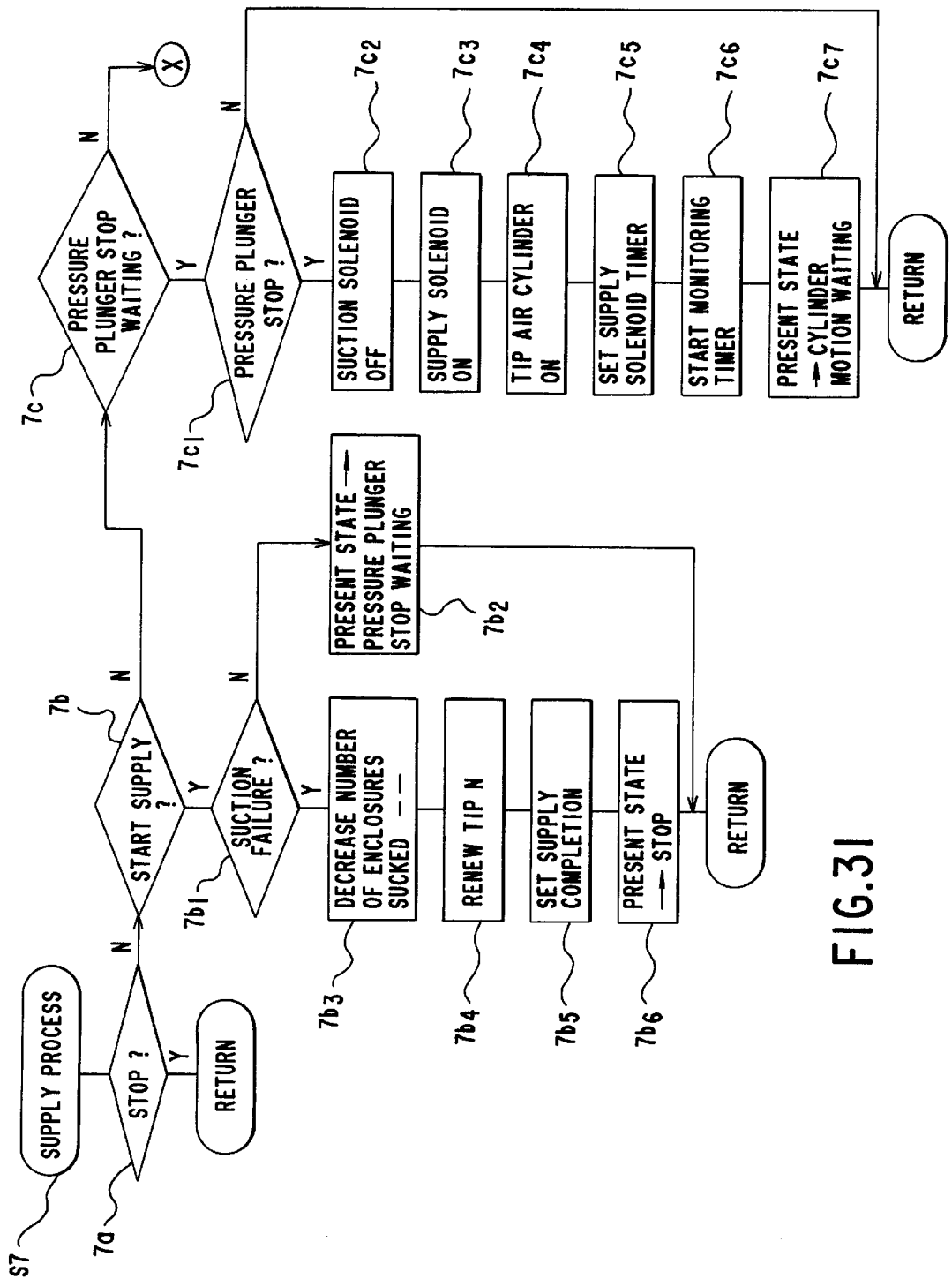
FIG. 31 is a flowchart showing a part of the supply process in FIG. 23 in detail.

At the supply process at step S7, as illustrated in FIG. 31, at first, whether or no the present state is stop state is judged at step S7a, and if the judgment is YES, the process returns to the main routine in the FIG. 23 and the process advances to the following step S8. Then, as shown in the state transition diagram in FIG. 34, when the rotary stop is set under the state that the present state is in initial positioning state, the present state is renewed with reference to the state transition diagram at step S11, so that the present is converted into supply start state. As described above, when the present state is in supply start state, the judgment at step S7a becomes NO, and the process advances to step S7b where whether or not the present state is turns to supply start state, and the judgment at step S7b becomes YES.

When the judgment at step S7b is YES, the process advances to step S7b1 to judge whether the tip does not suck an enclosure. If the judgment is NO, that is, if an enclosure is sucked, the process advances to step S7b2 to convert the present state from the supply start state to pressure plunger waiting state, and the process advances to step S8 in the main routine in the FIG. 23. If the judgment at step S7b1 is YES, that is, if an enclosure is not sucked, the process advances to step S7b3 to decrease the number of enclosures sucked, which is increased at step S6g3, and the process advances to step S7b4. At step S7b4, the number of the tip to which an enclosure is supplied next is renewed, and then the process advances to step S7b5 to set supply completion, and at step S7b6, the present state, which is in supply start state, is converted into stop state, and the process advances to step S8 in the main routine in the FIG. 23. If the judgment at step S7b1 is YES, that is, if an enclosure is not sucked, the number of enclosures sucked is decreased so as not to make a mistake in this number, and then supply completion is set without loss of supply motion.

After the present state is converted into pressure plunger stop waiting state at step S7b2, when the process enters the supply process at step S7, the judgment at steps S7a and S7b become NO, and the process advances to step S7c to allow the judgment at this step to become YES. When the judgment at step S7c becomes YES, the process advances to step S7c1 to judge whether or not the pressure plunger stop is set, and the judgment at step S7c1 is NO, the process advances to step S8 in the main routine in the FIG. 23. If the judgment at step S7c1 is YES, the process advances to step S7c2 to deenergize the suction solenoid, and the process advances to step S7c3 to energize the supply solenoid, which lowers the tip and supplies enclosures, and then the process advances to step S7c4 to energize the tip air cylinder.

Then, the process advances to step S7c5 to set the timer for deenergize the supply solenoid, and the process advances to step S7c6 to set the monitoring timer for restricting the operation time, and the process advances to step S6c7 to convert the present state from the pressure plunger stop waiting state to cylinder motion waiting state, and the process advances to step S8 in the main routine in the FIG. 23.

Figure 32:
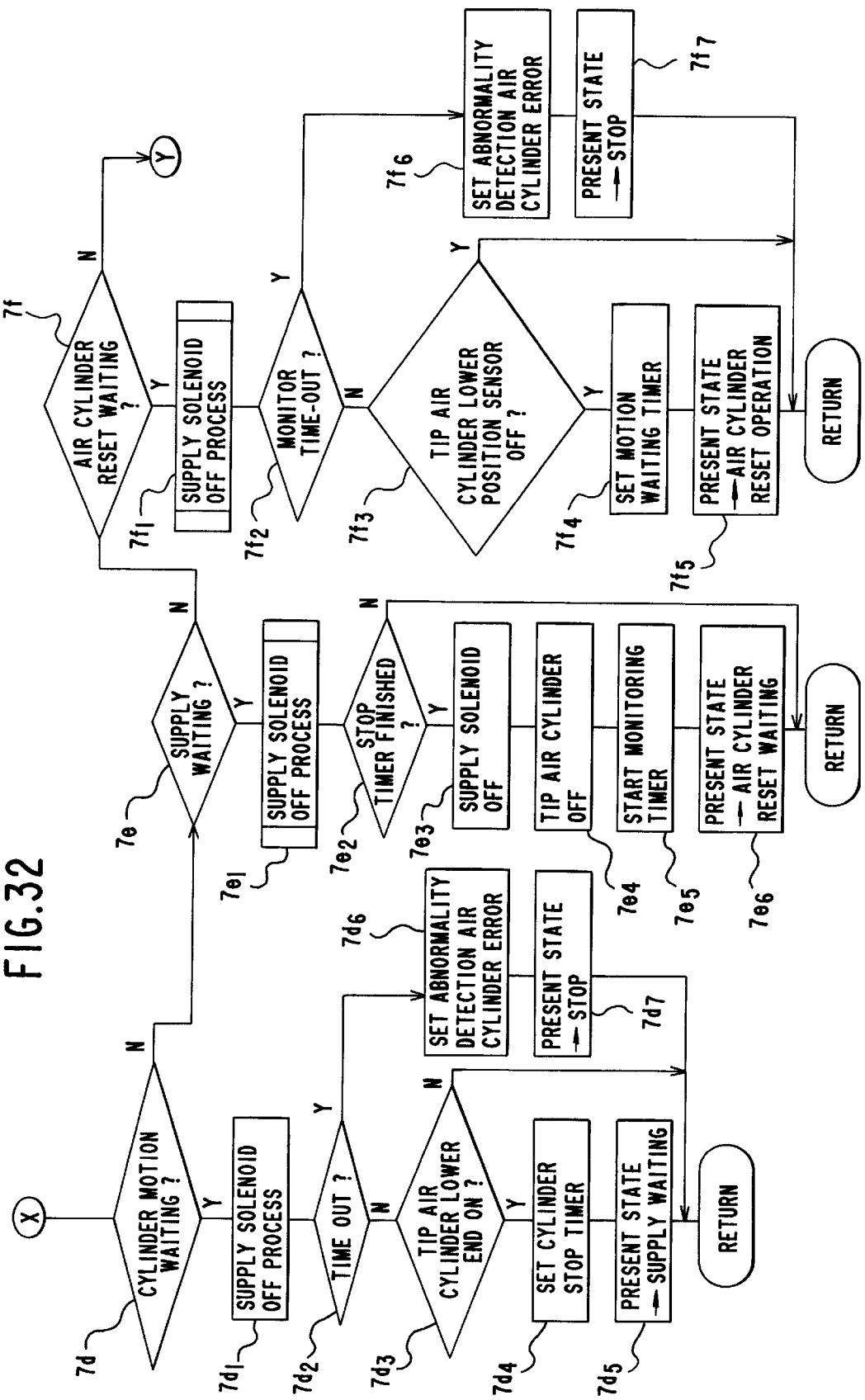
FIG. 32 is a flowchart showing another part of the supply process in FIG. 23 in detail.

As described above, after the present state is converted into the cylinder motion waiting state at step S7c7, when the process enters the suction process at step S7, the judgment at steps S7a to S7c become NO, and the process advances to step S7d in FIG. 32 to cause the judgment at this step to turn YES. When the judgment at step S7d becomes YES, the process advances to step S6d1 to deenergize the supply solenoid. In this solenoid OFF process, whether or not the supply solenoid timer causes time-out is judged. If time-out occurs, the supply solenoid is deenergized, and the process advances to step S7d2. At step S7d2, whether or not the monitoring timer, which is set at step S7c6, causes time-out is judged, and if the judgment is NO, the process advances to step S7d3. At step S7d3, whether or not the lower position detecting sensor of the tip air cylinder works is judged. If the judgment at step S7d3 is NO, the process advances to step S8 in the main routine in the FIG. 23. If the judgment at step S7d4 is YES, the process advances to step S7d4 to set tip air cylinder stop timer, and the process advances to step S7d5 to convert the present invention from the cylinder motion waiting state to supply waiting state, and the process advances to step S8 in the main routine in the FIG. 23.

When the judgment at step S7d2 is YES, the process advances to step S7d6 to set abnormality detection and to output the cylinder error, and at step S7d7, the present state, which is converted into the cylinder motion waiting state at step S7c7, is converted into stop state, and the process advances to step S8 in the main routine in FIG. 23.

As described above, after the present state is converted into the supply state at step S7d5, when the process enters the suction process at step S7, the judgment at steps S7a to S7d become NO, and the process advances to step S7e to cause the judgment at this step to turn YES. When the judgment at step S7e becomes YES, the process advances to step S7e1 to deenergize the supply solenoid. Then, the process advances to step S7e2 to judge whether or not the tip air cylinder stop timer which is set at step S7d4 is finished. If the judgment is NO, the process advances to step S8 in the main routine in the FIG. 23. If the judgment at step S7e2 is YES, the process advances to step S7e3 to deenergize the supply solenoid, and the process advances to step S7e4 to deenergize the tip air cylinder. Then, the process advances to step S7e5 to set the monitoring timer for restricting the operation time, and the process advances to step S7e6 to convert the present state from supply waiting state to air cylinder reset waiting state, and the process advances to step S8 in the main routine in the FIG. 23.

As described above, after the present state is converted into the air cylinder reset waiting state at step S7e6, when the process enters the suction process at step S7, the judgment at steps S7a to S7e become NO, and the process advances to step S7f to cause the judgment at this step to turn YES. When the judgment at step S7f becomes YES, the process advances to step S7f1 to judge whether or not the monitoring timer, which is set at step S7e5, causes timeout. If the judgment at step S7f2 is NO, the process advances to step S7f3 to judge whether or not the lower position detecting sensor of the tip air cylinder is deenergized. If the judgment at step S7f3 is NO, the process advances to step S8 in the main routine in the FIG. 23. If the judgment at step S7f3 is YES, the process advances to step S7f4 to set the motion waiting timer, and the process advances to step S7f5 to convert the present state from the air cylinder reset waiting state to air cylinder reset state, the process advances to step S8 in the main routine in the FIG. 23.

If the judgment at step S7f2 is YES, the process advances to step S7f6 to set abnormality detection and to output cylinder error, and at step S7f7, the present state, which is converted into air cylinder reset waiting state at step S7e6, is converted into stop state, and the process advances to step S8 in the main routine in the FIG. 23.

Figure 33B:
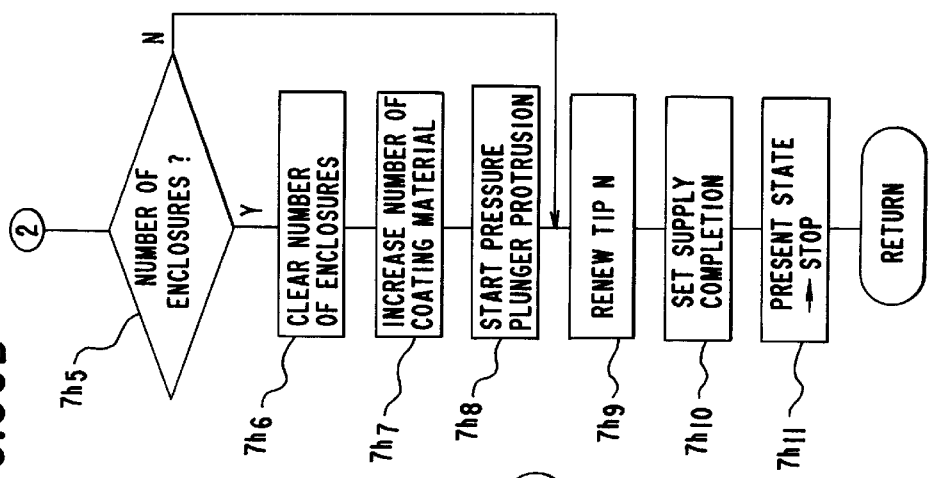
FIG. 33 is a flowchart of a further part of the supply process in FIG. 23 in detail.
Figure 33A:
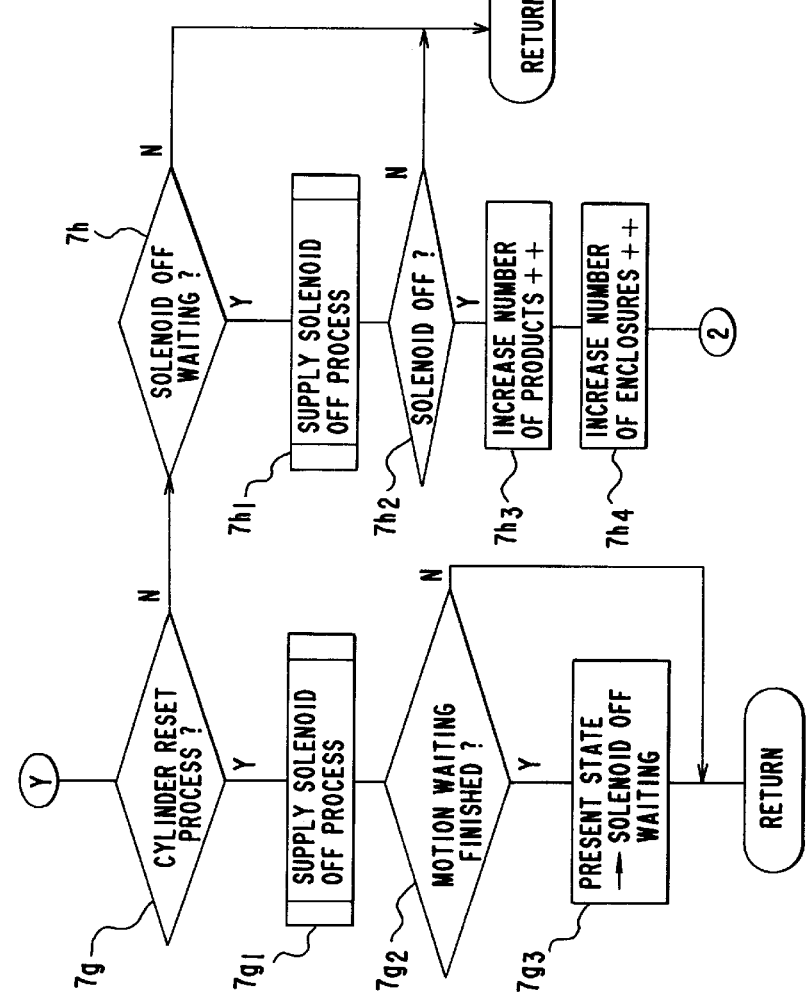

As described above, after the present state is converted into air cylinder reset state at step S7f5, when the process enters the suction process at step S7, the judgment at steps S7a to S7f become NO, and the process advances to step S7g in FIG. 33, and the judgment at this step becomes YES. When the judgment at step S7g becomes YES, the process advances to step S7g1 to deenergize the supply solenoid. Then, the process advances to step S7g2 to judge whether or not the motion waiting timer which is set at step S7f4 is finished. If the judgment is NO, the process advances to step S8 in the main routine in the FIG. 23. If the judgment at step S7g2 is YES, the process advances to step S7g3 to convert the present state from air cylinder reset waiting state to solenoid OFF waiting state, and the process advances to step S8 in the main routine in the FIG. 23.

As described above, after the present state is converted into solenoid OFF state at step S7g3, when the process enters the suction process at step S7, the judgment at steps S7a to S7g become NO, and the process advances to step S7h to deenergize the supply solenoid. Then, the process advances to step S7h2 to judge whether or not the supply solenoid is deenergized. If the judgment is NO, the process advances to step S8 in the main routine in the FIG. 23. If the judgment at step S7h2 is YES, the process advances to step S7h3 to increase the number of products, and the process advances to step S7h4 to increase the number of enclosures, and the process advances to step S7h5.

At step S7h5, whether or not the number of enclosures to be enclosed by one coating material reaches the setting. If the judgment is YES, the process advances to step S7h6 to clear the number of enclosures, and the process advances to step S7h7 to increase the number of coating material, and the process advances to step S7h8. At step S7h8, the motion of the pressure plunger starts, and the process advances to step S7h9 to renew the tip number, and the process advances to step S7h10. At the step S7h10, the supply completion is set, and the process advances to step S7h11 to convert the present state from solenoid OFF waiting state to stop state, and the process advances to step S8 in the main routine in the FIG. 23. In case that the judgment at steps S7a to S7h are NO, the process advances to step S8 in the main routine in the FIG. 23.

As described above, the process, which is explained with reference to the flow charts, starts operation after the position of the rotary plate (initial position), the upper position of the tip air cylinder, and the lower position of the supply rod are confirmed.

At first, the supply rod dips up an enclosure from custom liquid. The enclosure is put into a concave portion at the tip of the rod. In synchronization with the movement of the rod, the tip air cylinder with the tip 21 falls. The tip 21 is depressurized negative pressure source to suck an enclosure. The distance between the supply rod and the tip 21 is approximately 2 mm at the smallest, so that the tip 21 does not contact with the enclosure, however, the tip 21 sufficiently sucks the enclosure. In case that error occurs or the enclosure is not dipped up, the tip air cylinder and the supply rod return to original position, and this motion is repeated until the completion of the suction is confirmed.

When the completion of the suction is confirmed by a pressure switch attached to the tip air cylinder, the tip air cylinder rises; the supply rod falls; and the rotary plate rotates by 60 degrees by the stepping motor, and the same motions are repeated when the next tip 21 comes to the upside of the rod. The order of the rotation is already described above.

When initial motion is completed, whether or not an enclosure is sucked by the tip 21 is confirmed, and when an enclosure is sucked, the tip air cylinder, which comes to the upside of the nozzle plunger 8, falls. If an enclosure is not sucked, the rotary plate rotates until the tip 21 with an enclosure sucked, comes to the upside of the nozzle plunger 8. When the tip air cylinder falls to pass through the inside of the nozzle plunger 8, and the tip portion thereof moves in close to the coating material film, the tip 21 is pressurized and an enclosure is supplied. After the supply, the tip air cylinder rises, the pressure plunger stepping motor rotates, and the pressure plunger moves to extrude the coating material. Immediately after the pressure plunger is pushed to the valve main body, the check valve is closed, so that the coating material is discharged from the nozzle plunger 8. When the pressure plunger is drawn, the nozzle plunger 8 is closed and the check valve is opened to supply the coating material. This motion continues to manufacture an artificial seed. A beaker, or similar, which contains hardener, may be placed below the nozzle plunger 8 for further processing. The artificial seed manufacturing apparatus according to the present invention may be installed in a clean room or a clean bench, and control unit with sequencers may set operating state from outside, which permits continuous operation under aseptic state.

It is possible to move the pressure plunger after two enclosures are supplied through the setting of the control unit, so that the number of enclosures to be sucked may freely be changed. Further, the pressure plunger moves by the stepping motor, which can change the number of rotations through a driver set outside of the artificial seed manufacturing apparatus. As a result, the distance of the protrusion of the coating material and the diameter of the coating material becomes changeable. Moreover, after the enclosure is supplied to the tip, the pressure plunger moves, which provides product with enclosure without fail and no selection is needed after that.

As clearly understood from the explanation with reference to the flow charts in FIGS. 31 to 33, the CPU 101 functions as the stepping motor control means 101A to supply driving pulses for reciprocating the pressure plunger by the distance based on the setting data stored in the RAM 103A to the stepping motor. The RAM 103A works as distance storing means to erasably store setting data which are inputted through setting operation. Besides, the CPU 101 functions as the rotation control means 101B to move and stop the tip at the enclosure suction position and the enclosure supply position through driving source as well as the suction control means 101c to suck the enclosure which is supplied by the enclosure supplying mechanism to the tip at the enclosure sucking position. Further, the CPU 101 functions as supply control means 101D to supply the enclosure sucked by the tip which is supplied on the film of coating material through the hollow portion of the hollow nozzle plunger at the enclosure supply position.

The CPU 101, as the supply control means 101D, supplies enclosures on the film of coating material sucked by the tip through the hollow portion of the hollow nozzle plunger by the number based on setting data which is stored in the number of enclosure storing means 103B. The number of enclosures storing means 103B erasably stores the setting data, which is inputted through setting operation, for designating the number of enclosures to be supplied on the film of coating material. The CPU 101, as the stepping motor control means 101A, supplies a driving pulse for reciprocating the pressure plunger to the stepping motor, after the supply means 101D supplies the enclosures on the film of coating material.

Before causing the tip to supply enclosures at the enclosure supplying position, the CPU 101 as the supply means 101D, checks whether or not the tip sucks an enclosure. If the tip does not suck an enclosure, the CPU 101, does not allow the tip to conduct supplying operation and permits the next tip to conduct the supplying operation.

What is claimed is:

1. An artificial seed manufacturing apparatus comprising:
   an enclosure supply mechanism comprising:
   a container for accommodating enclosures;
   a tip for holding one enclosure of said enclosures in said container at a holding position and for supplying said one enclosure of said enclosures at a supplying position; and
   a driving source for driving said tip between said holding position and said supplying position;
   a coating material delivery mechanism comprising:
   a passage for accommodating a coating material;
   a pressure plunger slidably inserted into an insertion hole communicating with said passage, said pressure plunger being adapted to pressurize said coating material when moving forward to form a pressurized coating material and flowing said coating material into said passage when moving backward;
   a hollow nozzle plunger for opening a valve by said pressurized coating material to flow said coating material out of said valve, a part of said coating material flown out of said valve dropping due to gravity and a remainder of said coating material forming a film at a lower end portion of said hollow nozzle plunger; and
   a stepping motor for causing said pressure plunger to reciprocate through a rotation thereof in both directions; and
   a control unit for controlling said enclosure supply mechanism and said coating material delivery mechanism comprising:
   moving distance storing means for erasably storing setting data which are inputted through a setting operation to designate a moving distance of said pressure plunger; and
   stepping motor control means for supplying a driving pulse, said stepping motor control means allowing said pressure plunger to reciprocate by said moving distance, to said stepping motor based on said setting data stored in said moving distance storing means.

2. The artificial seed manufacturing apparatus as claimed in claim 1, wherein said control unit further comprises:
   rotation control means for allowing said tip to move to and stop at said holding position and said supplying position through said driving source;
   suction control means for allowing said tip to hold said one enclosure of said enclosures in said container at said holding position; and
- supply control means for supplying said one enclosure of said enclosures which is held by said tip on said film of said coating material through a hollow portion of said hollow nozzle plunger.

3. The artificial seed manufacturing apparatus as claimed in claim 2, wherein said control unit further comprises:

a number of enclosure storing means for erasably storing said setting data which are inputted through said setting operation to designate a number of said enclosures which should be supplied on said film of said coating material, wherein said supply control means supplies said one enclosure of said enclosures on said film of said coating material through said hollow portion of said hollow nozzle plunger by said number of said enclosures held by said tip based on said setting data stored in said number of said enclosure storing means; and said stepping motor control means supplies said driving pulse, which allows said pressure plunger to reciprocate, to said stepping motor after said supply control means supplies one of said enclosures on said film of said coating material through said hollow portion of said hollow nozzle plunger by said number of said enclosures.

4. The artificial seed manufacturing apparatus as claimed in claim 2, wherein said supply control means confirms whether said tip holds said one enclosure of said enclosures prior to a supplying motion of said tip at said supplying position, and if said tip does not hold said one enclosure of said enclosures, said supply control means causes said tip not to perform said supplying motion at said supplying position, but allows a following tip to conduct said supplying motion at said supplying position.

5. The artificial seed manufacturing apparatus as claimed in claim 1, wherein said supply control means confirms whether said tip holds said one enclosure of said enclosures prior to a supplying motion of said tip at said supplying position, and if said tip does not suck said one enclosure of said enclosures, said supply control means causes said tip not to perform said supplying motion at said supplying position, but allows a following tip to conduct said supplying motion at said supplying position.

6. The artificial seed manufacturing apparatus as claimed in claim 1, wherein one of said enclosures is held by said tip through suction.

7. An artificial seed manufacturing apparatus comprising:
   an enclosure supply mechanism comprising:
     a container for accommodating enclosures;
     a tip for holding one enclosure of said enclosures in said container at a holding position and for supplying said one enclosure of said enclosures at a supplying position; and
     a driving source for driving said tip between said holding position and said supplying position;
   a coating material delivery mechanism comprising:
     a passage for accommodating a coating material;
     a pressure plunger slidably inserted into an insertion hole communicating with said passage, said pressure plunger being adapted to pressurize said coating material when moving forward to form a pressurized coating material and flowing said coating material into said passage when moving backward;
     a hollow nozzle plunger for opening a valve by said pressurized coating material to flow said coating material out of said valve, a part of said coating material flown out of said valve dropping due to gravity and a remainder of said coating material forming a film at a lower end portion of said hollow nozzle plunger: and
     a stepping motor for causing said pressure plunger to reciprocate through a rotation thereof in both directions, and
   a control unit for controlling said enclosure supply mechanism and said coating material delivery mechanism comprising:
     moving distance storing means for erasably storing setting data which are inputted through a setting operation to designate a moving distance of said pressure plunger; and
     stepping motor control means for supplying a driving pulse, said stepping motor control means allowing said pressure plunger to reciprocate by said moving distance, to said stepping motor based on said setting data stored in said moving distance storing means; and wherein said enclosures together with culture liquid are accommodated in said container.

8. An artificial seed manufacturing apparatus comprising:
   an enclosure supply mechanism comprising:
     a container for accommodating enclosures;
     a tip for holding one enclosure of said enclosures in said container at a holding position and for supplying said one enclosure of said enclosures at a supplying position; and
     a driving source for driving said tip between said holding position and said supplying position;
   a coating material delivery mechanism comprising:
     a passage for accommodating a coating material;
     a pressure plunger slidably inserted into an insertion hole communicating with said passage, said pressure plunger being adapted to pressurize said coating material when moving forward to form a pressurized coating material and flowing said coating material into said passage when moving backward;
     a hollow nozzle plunger for opening a valve by said pressurized coating material to flow said coating material out of said valve, a part of said coating material flown out of said valve dropping due to gravity and a remainder of said coating material forming a film at a lower end portion of said hollow nozzle plunger; and
     a stepping motor for causing said pressure plunger to reciprocate through a rotation thereof in both directions; and
   a control unit for controlling said enclosure supply mechanism and said coating material delivery mechanism comprising:
     moving distance storing means for erasably storing setting data which are inputted through a setting operation to designate a moving distance of said pressure plunger; and
     stepping motor control means for supplying a driving pulse, said stepping motor control means allowing said pressure plunger to reciprocate by said moving distance, to said stepping motor based on said setting data stored in said moving distance storing means; and
   wherein said enclosures are adventive embryos.

* * * * *